US012629488B2

(12) United States Patent
Segal et al.

(10) Patent No.: US 12,629,488 B2
(45) Date of Patent: May 19, 2026

(54) NEBULIZER MONITORING DEVICE, SYSTEM AND METHOD

(71) Applicant: Pari Pharma GmbH, Starnberg (DE)

(72) Inventors: Michael Segal, Marlborough, MA (US); Nathan Arian Abel, Minneapolis, MN (US); Spencer Brown, Providence, RI (US); Everett Crosland, Marlborough, MA (US); Francisco Javier de Ana Arbeloa, Saint Paul, MN (US); Thomas Goodin, Marlborough, MA (US); Joseph Gordon, Mansfield, MA (US); Michael Metz, Minneapolis, MN (US); Daniel James Nelson, Ramsey, MN (US); Jae Hong Park, Providence, RI (US); Sean Scanlon, Minneapolis, MN (US); Janis Paulis Skujins, Minneapolis, MN (US); Jennet Toyjanova, Mansfield, MA (US)

(73) Assignee: PARI Pharma GmbH, Starnberg (DE)

( * ) Notice: Subject to any disclaimer, the term of this patent is extended or adjusted under 35 U.S.C. 154(b) by 254 days.

(21) Appl. No.: 17/860,454

(22) Filed: Jul. 8, 2022

(65) Prior Publication Data

US 2022/0339392 A1     Oct. 27, 2022

Related U.S. Application Data

(63) Continuation of application No. 16/390,908, filed on Apr. 22, 2019, now Pat. No. 11,406,786.

(51) Int. Cl.
*A61M 15/00* (2006.01)
*A61B 5/01* (2006.01)
(Continued)

(52) U.S. Cl.
CPC ........... *A61M 15/0021* (2014.02); *A61B 5/01* (2013.01); *A61B 5/0816* (2013.01); *A61B 5/087* (2013.01);
(Continued)

(58) Field of Classification Search
CPC .... A61M 11/00; A61M 11/005; A61M 11/06; A61M 15/00; A61M 15/001;
(Continued)

(56) References Cited

U.S. PATENT DOCUMENTS

| | | |
|---|---|---|
| 4,495,944 A | 1/1985 | Brisson et al. |
| 5,134,995 A | 8/1992 | Gruenke et al. |

(Continued)

FOREIGN PATENT DOCUMENTS

| | | |
|---|---|---|
| WO | 2011135353 A1 | 11/2011 |
| WO | 2015052519 A1 | 4/2015 |
| WO | 2017180980 A1 | 10/2017 |

OTHER PUBLICATIONS

International Search Report and Written Opinion dated Jul. 8, 2019, in connection with International Application No. PCT/US2019/028542.
(Continued)

*Primary Examiner* — Joseph D. Boecker
(74) *Attorney, Agent, or Firm* — Wolf, Greenfield & Sacks, P.C.

(57) ABSTRACT

Described herein are devices, systems and methods for monitoring the use of a nebulized medication, such as can be administered using a nebulizer. These can be used for monitoring a patient undergoing treatment for COPD and improve compliance to the recommended therapy. Monitored parameters include flow, humidity and acceleration and provide data as to the quantity and quality of nebulizer use.

28 Claims, 20 Drawing Sheets

(51) Int. Cl.

| | |
|---|---|
| *A61B 5/08* | (2006.01) |
| *A61B 5/087* | (2006.01) |
| *A61B 5/091* | (2006.01) |
| *A61M 11/00* | (2006.01) |
| *A61M 16/00* | (2006.01) |
| *A61M 16/14* | (2006.01) |
| *A61M 16/16* | (2006.01) |
| *G01F 1/34* | (2006.01) |
| *G01K 13/20* | (2021.01) |
| *G16H 20/13* | (2018.01) |

(52) U.S. Cl.
CPC ............. *A61B 5/091* (2013.01); *A61M 11/00* (2013.01); *A61M 16/024* (2017.08); *A61M 16/14* (2013.01); *G01F 1/34* (2013.01); *G01K 13/20* (2021.01); *G16H 20/13* (2018.01); *A61M 2016/0027* (2013.01); *A61M 2016/0039* (2013.01); *A61M 16/161* (2014.02); *A61M 2205/13* (2013.01); *A61M 2205/3368* (2013.01); *A61M 2205/3553* (2013.01); *A61M 2205/3584* (2013.01); *A61M 2205/583* (2013.01); *A61M 2205/587* (2013.01); *A61M 2205/8206* (2013.01); *A61M 2205/8243* (2013.01); *A61M 2230/40* (2013.01); *A61M 2230/42* (2013.01); *A61M 2230/50* (2013.01)

(58) Field of Classification Search
CPC .......... A61M 15/0021; A61M 15/0065; A61M 15/0086; A61M 2205/13; A61M 2205/3331; A61M 2205/3334; A61M 2205/3368; A61M 2205/52; A61M 2205/583; A61M 2205/587; A61M 2205/60; A61M 16/024; A61M 2016/0039; A61M 2230/40; A61M 2230/42; A61M 2230/50; A61B 5/01; A61B 5/0816; A61B 5/087; A61B 5/091; G16H 20/13; G01K 13/20
See application file for complete search history.

(56) References Cited

U.S. PATENT DOCUMENTS

| | | | |
|---|---|---|---|
| 5,277,175 A | 1/1994 | Riggs et al. | |
| 5,363,842 A | 11/1994 | Mishelevich et al. | |
| 5,392,768 A | 2/1995 | Johansson et al. | |
| 5,570,682 A | 11/1996 | Johnson | |
| 5,743,250 A | 4/1998 | Gonda et al. | |
| 5,794,612 A | 8/1998 | Wachter et al. | |
| 5,865,171 A | 2/1999 | Cinquin | |
| 5,964,223 A | 10/1999 | Baran | |
| 6,076,519 A | 6/2000 | Johnson | |
| 6,205,999 B1 | 3/2001 | Ivri et al. | |
| 6,283,923 B1 | 9/2001 | Finkelstein et al. | |
| 6,390,088 B1 | 5/2002 | Nohl et al. | |
| 6,530,370 B1 | 3/2003 | Heinonen | |
| 6,745,764 B2 | 6/2004 | Hickle | |
| 6,871,535 B2 | 3/2005 | Blakley et al. | |
| 6,958,691 B1 | 10/2005 | Anderson et al. | |
| 8,333,190 B2 | 12/2012 | Addington et al. | |
| 8,807,131 B1 | 8/2014 | Tunnell et al. | |
| 9,060,715 B2 | 6/2015 | Schipper et al. | |
| 9,550,031 B2 | 1/2017 | Van Sickle et al. | |
| 11,406,786 B2 | 8/2022 | Segal et al. | |
| 2003/0205229 A1* | 11/2003 | Crockford | A61P 11/06 128/200.23 |
| 2006/0048772 A1 | 3/2006 | Borgschulte | |
| 2006/0130838 A1* | 6/2006 | Lee | A61B 5/087 128/200.23 |
| 2007/0023034 A1* | 2/2007 | Jongejan | A61M 15/009 128/200.14 |

| | | | |
|---|---|---|---|
| 2011/0000481 A1 | 1/2011 | Gumaste et al. | |
| 2013/0008436 A1 | 1/2013 | Von Hollen et al. | |
| 2013/0053719 A1 | 2/2013 | Wekell | |
| 2014/0142456 A1 | 5/2014 | Fischer et al. | |
| 2014/0350367 A1 | 11/2014 | Subramaniam | |
| 2014/0352690 A1 | 12/2014 | Kolb et al. | |
| 2015/0099994 A1* | 4/2015 | Spencer | A61M 15/0085 600/533 |
| 2015/0273165 A1 | 10/2015 | Hadash | |
| 2016/0105047 A1 | 4/2016 | Cui | |
| 2016/0144141 A1 | 5/2016 | Biswas et al. | |
| 2016/0287139 A1 | 10/2016 | Luttrell | |
| 2016/0325058 A1* | 11/2016 | Samson | A61B 5/0022 |
| 2016/0331022 A1 | 11/2016 | Cameron | |
| 2016/0331037 A1 | 11/2016 | Cameron | |
| 2016/0334119 A1 | 11/2016 | Cameron | |
| 2016/0346489 A1 | 12/2016 | Finke et al. | |
| 2016/0354562 A1 | 12/2016 | Morrison | |
| 2017/0027232 A1 | 2/2017 | Scheck et al. | |
| 2017/0047748 A1 | 2/2017 | Blyde et al. | |
| 2017/0079557 A1* | 3/2017 | Lauk | A61B 5/74 |
| 2017/0085116 A1 | 3/2017 | Tsao | |
| 2017/0270260 A1* | 9/2017 | Shetty | G16H 40/67 |
| 2018/0008790 A1 | 1/2018 | Costella et al. | |
| 2018/0279918 A1* | 10/2018 | Hagen | A61B 5/6887 |
| 2018/0317557 A1 | 11/2018 | Monsees et al. | |
| 2019/0060590 A1* | 2/2019 | Starr | A61B 5/0022 |
| 2019/0240428 A1 | 8/2019 | Stenzler et al. | |
| 2020/0276398 A1 | 9/2020 | Hebrank et al. | |

OTHER PUBLICATIONS

International Preliminary Report on Patentability dated Nov. 4, 2021, in connection with International Application No. PCT/US2019/028542.

"A few Android Phones that have Temperature Sensor"; retrieved from https://web.archive.org/web/20160926111008/https://webcusp.com/a-few-android-phones-that-have-temperature-sensor with date Sep. 13, 2016 (only pertinent pages provided).

"Asthma in adults" University of Maryland Medical Center (2017) https://umm.edu/health/medical/reports/articles/asthmainadults.

"Chronic Obstructive Pulmonary Disease (COPD)""—Cedars Sinai https://www.cedarssinai.edu/Patients/HealthConditions/ChronicObstructivePulmonaryDiseaseCOPD.Aspx (2017)".

"Chronic Obstructive Pulmonary Disease (COPD)" Centers for Disease Control and Prevention.

"Chronic obstructive pulmonary disease" University of Maryland Medical Center (2017) https://umm.edu/health/medical/reports/articles/chronicobstructivepulmonarydisease.

"Chronic Obstructive PulmonaryDisease (COPD)"" Fact Sheet—National Institutes of Health (2010)".

"Public Health Strategic Framework for COPD Prevention" CDC (2011).

Agh et al., "Adherence to therapy in chronic obstructive pulmonary disease." Chronic obstructive pulmonary disease—current concepts and practice. Rijeka, Croatia: InTech (2012): 275-290.

Agusti et al., "Night-time symptoms: a forgotten dimension of COPD." European Respiratory Review 20.121 (2011): 183-194.

Allen-Ramey et al., "Patient characteristics, treatment patterns, and health outcomes among COPD phenotypes." International journal of chronic obstructive pulmonary disease 7 (2012): 779-787.

Anderson et al., "Technology Device Ownership: 2015", Pew Research Center (2015): 1-26.

Ari "Jet, ultrasonic, and mesh nebulizers: an evaluation of nebulizers for better clinical outcomes." Eurasian J. Pulmonol (2014) 16: 1-7.

Aryal et al., "Influence of sex on chronic obstructive pulmonary disease risk and treatment outcomes." International journal of chronic obstructive pulmonary disease 9 (2014) 9: 1145-1154.

Boyter et al., "How do patients use their nebuliser in the community?. " Respiratory medicine 99.11 (2005): 1413-1417.

Copley "Nebulizer Testing: Exploring the implications of new regulatory guidance for testing nebulizers", Inhalation Magazine (2008).

(56) References Cited

OTHER PUBLICATIONS

Dennis "Standardization Issues: In Vitro Assessment of Nebulizer Performance", Respitory Care 47.12 (2002) 1445-1458.

Dolce et al., "Medication adherence patterns in chronic obstructive pulmonary disease." Chest 99.4 (1991): 837-841.

Evensen et al., "Management of COPD exacerbations." American family physician 81.5 (2010): 607-613.

Gardenhire et al., "A Guide to Aerosol Delivery Devices for Respitory Therapists" 3rd Edition (2013).

Harvey et al., "Comparison of jet and ultrasonic nebulizer pulmonary aerosol deposition during mechanical ventilation." European Respiratory Journal 10.4 (1997): 905-909.

Helvoort et al., "Respiratory constraints during activities in daily life and the impact on health status in patients with early-stage COPD: a cross-sectional study." NPJ primary care respiratory medicine 26.1 (2016): 1-7.

Hess et al., "Medication nebulizer performance: effects of diluent volume nebulizer flow, and nebulizer brand." Chest 110.2 (1996): 498-505.

Janssens et al., "Inspiratory flow rates at different levels of resistance in elderly COPD patients." European Respiratory Journal 31.1 (2008): 78-83.

Johns et al., "Nebulisers: their effectiveness, indications and limitations." Prescriber 18.3 (2007): 16-28.

Kikidis et al., "The digital asthma patient: the history and future of inhaler based health monitoring devices." Journal of aerosol medicine and pulmonary drug delivery 29.3 (2016): 219-232.

Laforest et al., "Correlates of adherence to respiratory drugs in COPD patients." Primary Care Respiratory Journal 19.2 (2010): 148-154.

Madan et al., "Expired air temperature at the mouth during a maximal forced expiratory manoeuvre." European Respiratory Journal 6.10 (1993): 1556-1562.

Nici "Exacerbation of COPD"Am J Respir Crit Care Med vol. 189, p. 11-p. 12, (2014).

O'CALLAGHAN et al., "The Science of nebullsed drug delivery" Thorax 52.2 (1997) S31-S44.

Peacock et al., "Outdoor air pollution and respiratory health in patients with COPD." Thorax 66.7 (2011): 591-596.

Poushter "Smartphone ownership and internet usage continues to climb in emerging economies." Pew Research Center 22 (2016): 1-44.

Prabhakar et al., "Online sample conditioning for portable breath analyzers." Analytical chemistry 84.16 (2012): 7172-7178.

Qureshi et al., "Chronic obstructive pulmonary disease exacerbations: latest evidence and clinical implications." Therapeutic advances in chronic disease 5.5 (2014): 212-227.

Restrepo et al., "Medication adherence issues in patients treated for COPD." International journal of chronic obstructive pulmonary disease 3.3 (2008): 371-384.

Ricard "Are we really reducing tidal volume—And should we?" Am J Resp Care Med 167 (2003): 1297-1298.

Smith et al., "US smartphone use in 2015." Pew Research Center 1-59 (2015).

Stanescu et al., "Maximal inspiratory flow rates in patients with COPD." Chest 118.4 (2000): 976-980.

Tashkin "A review of nebulized drug delivery in COPD." International journal of chronic obstructive pulmonary disease 11 (2016): 2585-2596.

"Thomas et al., ""No room to breathe: the importance of lung hyperinflationin COPD"" Prim Care Respir J 2013; 22 (1): 101-111".

"Toy et al., ""Treatment of COPD: Relationships between dailydosing frequency, adherence, resource use, andcosts"" Respiratory Medicine (2011) 105, 435e441".

Van Geffen et al., "Diagnosing viral and bacterial respiratory infections in acute COPD exacerbations by an electronic nose: a pilot study." Journal of breath research 10.3 (2016): 036001, 1-7.

Vinuraja et al., "Smart Phone-Based Peak Expiratory Flow Meter." Asian Journal of Applied Science and Technology (AJAST) 1.2 (2017): 151-153.

"Watson et al., ""Gender differences in the managementand experience of Chronic ObstructivePulmonary Disease"" Respiratory Medicine (2004) 98, 1207-1213".

Wedzicha et al., "Exacerbations of chronic obstructive pulmonary disease." Respiratory care 48.12 (2003): 1204-1215.

Williams et al., "A pilot study quantifying the shape of tidal breathing waveforms using centroids in health and COPD." Journal of clinical monitoring and computing 28.1 (2014): 67-74.

* cited by examiner

NEBULIZER MONITORING DEVICE, SYSTEM AND METHOD

CROSS-REFERENCE TO RELATED APPLICATION

This application is a Continuation under 35 U.S.C. § 120 of U.S. application Ser. No. 16/390,908 filed on Apr. 22, 2019, now U.S. Pat. No. 11,406,786, claims any and all benefits of the prior application as provided by law, and the contents of the earlier filed application is herein incorporated by reference in its entirety.

STATEMENT REGARDING FEDERALLY SPONSORED RESEARCH

Not Applicable.

TECHNICAL FIELD

This invention generally relates to devices, systems and methods for monitoring the use of a nebulized medication, such as can be administered using a nebulizer.

BACKGROUND

Nebulizers are drug delivery devices that are used to deliver a medication, that is in the form of a solution or a suspension, to the airways by aerosolizing the solution so that it can be breathed in by a patient. The size of the particles in the aerosol for delivery of the medication to the lungs is an important parameter to control. Particles larger than about 5 μm diameter are more likely than smaller particles to deposit in the upper airways and then are swallowed rather than being deposited in the lungs. Conversely, particles smaller than about 1 μm diameter may simply be inhaled and exhaled with minimal deposition in the lungs. Therefore, nebulizers are designed for delivery of particles typically between about 1 μm and 5 μm which is the desired particle size range that generally comprises the reparable fraction of inhaled bronchodilators.

Most commonly, a nebulizer produces an aerosol by forming particulates or "atomization" of the medical solution or suspension by either using a pressurized gas source, as in a "jet" nebulizer, or by using ultrasonic energy, as in an "ultrasonic" nebulizer and an "electronic" or "mesh" nebulizer. The jet nebulizer uses the Venturi effect and typically requires a predefined flow rate (e.g., 2 to 10 L/min) of pressurized gas to draw the solution up through a capillary tube from a nebulizer reservoir containing the drug solution or suspension in order to generate a wide range of particle sizes. These initial liquid particles are blasted into one or more baffles, which take larger particles out of the aerosol and return them to the reservoir, while allowing delivery of the smaller particles to the user who inhales these through a mouthpiece. Ultrasonic nebulizers use an ac electric power source to vibrate a piezoelectric element in a nebulizer reservoir, creating standing waves on the surface of the solution/suspension. Small droplets break free from the solution due to these waves and are released as an aerosol with large and small particles that are culled to small particles by baffles, as in the jet nebulizer. The aerosol can then be delivered to the lungs as previously described. Mesh nebulizers use a vibrating piezoelectric element coupled to a fine mesh to generate the aerosol and control the particle size with the mesh sizing. (R. Johns et al., *Prescriber* 2007, 5, 16-28; D. S. Gardenhire et al., A Guide to Aerosol Delivery Devices for Respiratory Therapists, 3<sup>rd</sup> ed., American Association for Respiratory care, ©2013).

There are many potential indications for nebulizer therapy such as bronchial narrowing, airway inflammation, viscous retained secretions, airspace infection and colonization, dyspnoea and chronic coughing. Alleviation of these symptoms/conditions includes administering a nebulized drug such as bronchodilator drugs (e.g., as salbutamol, terbutaline and ipratropium), anti-inflammatory drugs (e.g., budesonide and fluticasone), secretion disintegrators (e.g., saline and DNase/dornase), antimicrobials (e.g., pentamidine), long-acting bronchodilators (e.g., formoterol, arformoterol, glycopyrrolate and revefenacin), and pain management medications (e.g., morphine and lidocaine). These symptoms/conditions can occur due to disease settings such as chronic obstructive pulmonary disease (COPD), asthma, cystic fibrosis, bronchiectasis, HIV, lung cancer or combinations of these. COPD refers to a progressive condition that can result from a number of diseases states, most frequently emphysema, chronic bronchitis and some asthma sufferers. COPD is a disease that typically occurs in male and female patients≥40 years of age and is associated with a high disease burden including reduced quality of life, impaired functioning and significant direct and indirect costs. There is currently no cure of COPD, only management of the symptoms as a patient's lung oxygenation capacity decreases over the continuum of the disease. (J. L. Peacock et al. *Thorax* 2011, 66, 591-596; A. Agusti *Eur. Repir Rev* 2011, 121m 183-194; E. L. Toy et al., *Respiratory Medicine,* 2011, 105, 435-441).

It is critically important in COPD management for patients to adhere to inhaled medications therapies, a central part of which is the use of bronchodilators, which includes beta-agonists, anti-cholinergic, and methylxanthines (e.g., theophylline) delivered by a nebulizer. To date compliance is based on self-reporting, reported symptom assessments and spirometry to assess if dosing is effective. There is wide variability in patient compliance with prescribed COPD medicines, symptom reporting and many physicians diagnose and manage COPD patients based on symptom presentation and medical history without a spirometric assessment. An estimate of 50% compliance to a prescribed therapy might be considered high. Patients having COPD can periodically also have an acute exacerbation of the COPD symptoms. These are caused by inflammations which lead to narrowing and accumulation of mucus in airways. The cause of these exacerbations is not always known although many cases are due to viral and bacterial infections in the lungs. Exacerbations can also occur from inhaling irritating substances from the environment such as from air pollution or from pollen or other allergens. The inflammation (irritation and swelling) in the lungs during and after an exacerbation of COPD can often lead to a protracted recovery, worsening of co-morbidities and death of a patient. Early detection of exacerbation is often dependent on patient reporting. Patients with COPD also require adequate education on the disease process, such as exacerbations and comorbidities, and also on the use of different medications and devices.

Treatment of COPD can often also include significant economic burdens and behavioral and lifestyle changes such as starting a smoking cessation program, adhering to an exercise program (i.e. pulmonary rehabilitation), and becoming dependent on breathing supplemental oxygen both within and outside of the home. In addition, the demography of these patients also means that it is likely they may have other medical treatments and therapies to keep track of, further burdening their ability to comply with any therapy. It is therefore not surprising, although distressing, that adherence to COPD therapy is poor. Patients can be clustered into four general categories of adherence to inhaled therapies; (1) regular use with good technique, (2) regular use with poor technique, (3) irregular use with good technique, and (4) irregular use with poor technique. It has been found that patients with irregular use, and poor techniques (category 4), have the highest mortality and patents with irregular use and good technique (category 3) have the second highest mortality (but about half that of category 4) and the highest incidence of exacerbations. Patients with regular use but poor techniques (category 2) have better outcomes with a small increase in the rate of exacerbations. Not surprisingly, patients with regular use and good techniques have the lowest mortality and exacerbations. Therefore, the adherence behaviors are associated with specific clinical outcomes, where regular (e.g., prescribed, the quantity of use) use is the most important factor and proper use (e.g., the quality of use) is a lesser but still important factor. (Cushen et al., AJRCCM Articles in Press, 19 Jan. 2018; Arzu Ari *Eurasian J. Pulmonol*, 2014, 16, 1-7; S. Lareau et al., *Am J. Respir. Crit. Care Med.*, 2014, 189, P11-P12; Tamas Agh et al. Chronic Obstructive Pulmonary Disease—Current Concepts and Practice, InTech, 2012, Ch. 12, 275-290; R. D. Restrepo et al., *International Journal of COPD*, 2008, 3(3), 371-384).

While treatments for COPD are available, there is a need for improving patient compliance to the prescribed inhalation treatment. In addition, early detection of an exacerbation will greatly improve the ability to adequately treat and stabilize patients. Improvement of compliance and early detection of an exacerbation has the potential to significantly decrease the costs of treatments as well as attenuate lung function decline, improve quality of life for COPD sufferers and is recognized as an unmet need in this treatment therapy.

There is also a need for the monitoring of the use of a nebulized drug in tests, such as for collecting data in a clinical trial. Currently the standard method in these tests if for the user to fill in a daily log as to the use of the drug. As in COPD, compliance to the instructions given to subject in the drug test is hard or possibly harder to verify than with COPD since the administered drug might be a placebo and no effect would be seen to indicate non-compliance in the study. Additionally, unreliable compliance reporting by user in a clinical trial may confound the true effect of a drug candidate on physiological endpoint data (e.g. forced expiratory volume in one second; $FEV_1$) that is utilized to characterize the drug for evaluation by sponsors, approval by regulators and ultimately use by health care providers to treat COPD patients. Improvement in data collection and data breadth for nebulizer use and medication is therefore another unmet need.

SUMMARY OF THE INVENTION

Generally, the invention relates to a nebulizer monitoring device, a system including the nebulizer device and methods of monitoring a user's nebulizer use using the monitoring device and system. In accordance with some embodiments, the devices, systems and methods provide measurements of flow, humidity, temperature and movement by sensors disposed in or with the nebulizer which can be used to monitor a user's real time use of the nebulizer. In addition, the data can be collected and processed into data such as tidal volume, breathing rate and body temperature for visualization by a user, care giver and health care provider. For example, the data can be used for data collection related to usage compliance, for an experimental study or for tracking or detection of a response to an inhaled respiratory drug and onset of an exacerbation. The device, system and methods accordingly aid in facilitating compliance of nebulizer use according to a prescribed therapy regime as well as providing real time monitoring of a user and onsets of exacerbations.

In one aspect, the invention relates to a nebulizer system that includes a subsystem for detecting and tracking the use of the nebulizer by a user. The system can include one or more sensors configured to detect and measure the flow of nebulized medication through the nebulizer and a controller configured to record and report the usage of the nebulizer by the user. The base substrate having a first surface and a second surface, and an integrated circuit mounted to the second surface of the base substrate.

In accordance with some embodiments of the invention there is provided a nebulizer monitoring device. The device comprises a first connector adapted to engage a nebulizer mount and a second connector adapted to engage a nebulizer mouthpiece. The device also comprises a conduit having an inner surface forming a fluid connection between the first connector and the second connector. A flow sensor is disposed in the conduit and between the first connector and the second connector, and the flow sensor is configured to measure a flow rate vector of fluid in the conduit. At least one indicator is connected to the flow sensor, and at least one controller is connected to the flow sensor and the first indicator whereby at least one dimension of the at least one indicator changes as a function of a measured flow rate vector. In some options of the device the flow sensor includes a differential pressure sensor or a flow meter.

Optionally the nebulizer device includes at least one light source, for example, wherein the change in the dimension of the at least one indicator includes a change in intensity of light emitted from the at least one light source. In some embodiments the at least one light source comprises a first light emitting diode (LED) and the change in intensity of light emitted by the first LED changes as function of the measured fluid flow rate vector. Optionally, the at least one indicator includes a second LED light having a different color than that of the first LED light and the first light is illuminated when the measured fluid flow rate vector is in a first direction, and the second light is illuminated when the measured fluid flow rate vector is in a second direction. Optionally, the at least one light source comprises at least two light emitting diodes (LEDs) and a change in the dimension of the at least one indicator includes a change in the state of at least one of the two LEDs. Optionally, the at least one light source includes an array of LEDs that are illuminated in sequence such that the indicator is perceived as a lengthening indicator and the perceived lengthening is a function of the measured flow rate vector, and wherein a direction of lengthening indicates the vector direction of the measured flow rate vector.

Optionally, the first indicator of the nebulizer monitoring device comprises an audible indicator comprising at least one sound emitting device. In some other embodiments the dimension of the audible indicator is one or more of amplitude, frequency and pattern of sound emitted by the at least one sound emitting device. For example, the sound can change from loud to soft, soft to loud, low to high, high to low, the sound can emit beeping that changes in duration and/or frequency, the sound can emit two or more sounds that are perceived as being simultaneously emitted (e.g., a chord), the sound can also be musical (e.g., a song or song snippet). Also optionally, the first indicator comprises a tactile indicator comprising one or more of vibrating devices, radiant heat devices and topography changing devices. Examples include, wherein the indicator provides a tactile sense of vibration when the device is held and a dose is complete, or a display that can be read by the visually impaired (e.g., braille). Optionally, the tactile indicator includes a vibrating device and the dimension of the audible indicator includes one or more of intensity and frequency of a vibration.

The nebulizer monitoring device can also optionally further include a humidity sensor disposed in or connected to the conduit between the nebulizer mount and the mouth piece and configured to measure humidity in the conduit; whereby at least one dimension of the at least one indicator changes as a function of the measured flow rate vector and the measured humidity from the humidity sensor.

The nebulizer monitoring device can also optionally further comprise a usage indicator including an array of light emitting diodes (LEDs) connected to the at least one controller. In some optional embodiments, the at least one controller is configured to: turn off all LEDs of the usage indicator at a predefined time; turn on one LED of the usage indicator in a predefined order after the controller receives a plurality of measured flow rate vectors from the flow sensor for a predefined minimum time followed by a measure of no flow rate vector by the flow sensor for a predefined time. Optionally, the controller is configured to: turn off all LEDs of the usage indicator at a predefined time; turn off all LEDs of the usage indicator at a predefined time; turn on one LED of the usage indicator in a predefined order after the controller receives measured flow rate vectors indicating flow (e.g., in a first direction and optionally a second direction), and the controller receives a plurality of measures of humidity over a predefined amount of time and wherein the average of the plurality of measures of humidity over the predefined time is above a predefined threshold. Optionally, the usage indicator can include a visual indicator comprising an array of LED lights wherein each dose taken after a designated start time is indicated by a sequential illumination of an LED in the array, and the array is reset by turning off of all of the LEDs at a predefined time of day. Optionally, the predefined threshold is a relative humidity of 80%.

Additionally, and optionally, the device can further comprise a temperature sensor configured to contact at least one lip of a user, when the device is in use for administering a medication to the user, and wherein the at least one controller is connected to the temperature sensor. Optionally, the temperature sensor is disposed at a first end of the mouthpiece that is configured for insertion in the user's mouth, such that when the user inserts the mouthpiece into their mouth, the temperature sensor is positioned to measure a temperature of at least a portion of the user's lip. Optionally, the second connector extends along a first axis and further comprises an arm extending along the first axis outside the conduit such that the arm extends along the mouthpiece when the mouthpiece is connected to the second connector; and wherein a first portion of the arm includes the temperature sensor, and a second portion of the arm is connected to the conduit and connects the temperature sensor to the at least one controller. Also optionally the first portion of the arm is configured to align with the mouthpiece such that the first portion of the arm contacts at least a portion of the user's lip when the user inserts the mouthpiece into their mouth. The arm can optionally include a hinge connecting the arm to the conduit. The arm can also optionally have a flexible tether to allow an extension to the length of the arm to the conduit. In some embodiments the temperature sensor includes a thermistor.

Optionally the nebulizer device further comprises an accelerometer connected to the at least one controller. Also optionally, the nebulizer device further comprises a battery connected to the at least one controller, and a charging circuit for charging said battery. Optionally the battery charging circuit includes an induction coil configured for inductive charging.

In accordance with some other embodiments of the invention there is provided a system for nebulizer use comprising the nebulizer monitoring device and a base station in wireless communication with the nebulizer monitoring device. Optionally the nebulizer monitoring device includes a battery connected to the at least one controller, and a charging circuit for charging said battery. The base station also optionally includes a port configured to receive the nebulizer monitoring device and for charging of the nebulizer monitoring device. Optionally, the base station includes an induction coil and the nebulizer monitoring device includes an induction coil such that when the nebulizer monitoring devices is received by the base station, the base station inductively charges the nebulizer monitoring device. In some optional embodiments, the base station includes a plurality of pogo-pins and the nebulizer monitoring device includes a plurality of electric contact pads, such that when the nebulizer monitoring device is received by the base station, at least two pogo-pins of the base station make contact with two contact pads of the nebulizer monitoring device and transfer electrical energy to the nebulizer monitoring device to charge the battery.

Optionally, the base station of the system for nebulizer use includes at least one environmental monitoring sensor and a controller connected to the at least one environmental monitoring sensor configured to receive and store environmental sensor data from the at least one environmental monitoring sensor. Optionally, the at least one environment monitoring sensor includes at least one of a VOC sensor, a $CO_2$ sensor, a humidity sensor, a temperature sensor, mold sensor, pollen sensor, spore sensor, bacteria sensor and a particulate sensor. Optionally, the base station includes a network interface such that the base station can transfer data to a remote computer system. Also optionally, the remote computer system includes at least one processor and associated member and is configured to receive and store data from the base station.

In accordance with another embodiment of the invention there is provided a method for administering to a user a nebulized medication, the method comprising administering a nebulizer therapy regime of a prescribed dosage of said medication using a nebulizer that includes the nebulizer monitoring device or the system for nebulizer use. Optionally, the user is a patient in need of a nebulized medication and is at a high risk of non-compliance to the nebulizer therapy regime. Also optionally, the user is a subject in a drug study or drug trial. In some options, one or more usage indicators are stored in electronic form. In some embodiments the one or more usage indicators are displayed on a data visualization system and a care provided or the user views the one or more indicators on the visualization system and if one or more indicators is indicative of an incorrect use of the device or an exacerbation, a corrective action is taken by the user or health care provider. Also optionally, the usage indicators are selected from the group consisting of temperature, respiration rate, tidal volume, dosage and orientation of the device, and combinations thereof. Optionally, each of the usage indicators comprise a plurality of usage indicators which are time stamped.

These and other capabilities of the invention, along with the invention itself, will be more fully understood after a review of the following figures, detailed description, and claims.

BRIEF DESCRIPTION OF THE DRAWINGS

The accompanying drawing figures, which are incorporated into this specification, illustrate one or more exemplary embodiments of the inventions and, together with the detailed description, serve to explain and illustrate the principles and applications of these inventions. The drawings and detailed description are illustrative, and not limiting, and can be adapted and modified without departing from the scope and spirit of the inventions.

FIG. 2C shows 15 breaths per minute and FIG. 2D shows 20 breaths per minute.

FIG. 3A Panel 1 shows the thermistor not in contact with the mouthpiece, FIG. 3A Panel 2 shows the thermistor in contact with the mouthpiece.

FIG. 3B Panel 1 shows the thermistor not in contact with the mouthpiece, FIG. 3B Panel 2 shows the thermistor in contact with the mouthpiece FIG. 3C Panel 1 shows the thermistor not in contact with the mouthpiece, FIG. 3C Panel 2 shows the thermistor in contact with the mouthpiece

FIG. 4B Panel 1 shows that during inhale the LED ramps brighter. FIG. 4B Panel 2 shows that during exhale the LED light dims.

FIG. 5C panel 1 shows a green light emission indicating an inhale, while FIG. 5C panel 2 show a purple light emission indicating an exhale.

DETAILED DESCRIPTION OF THE ILLUSTRATED EMBODIMENTS

Figure 1A:
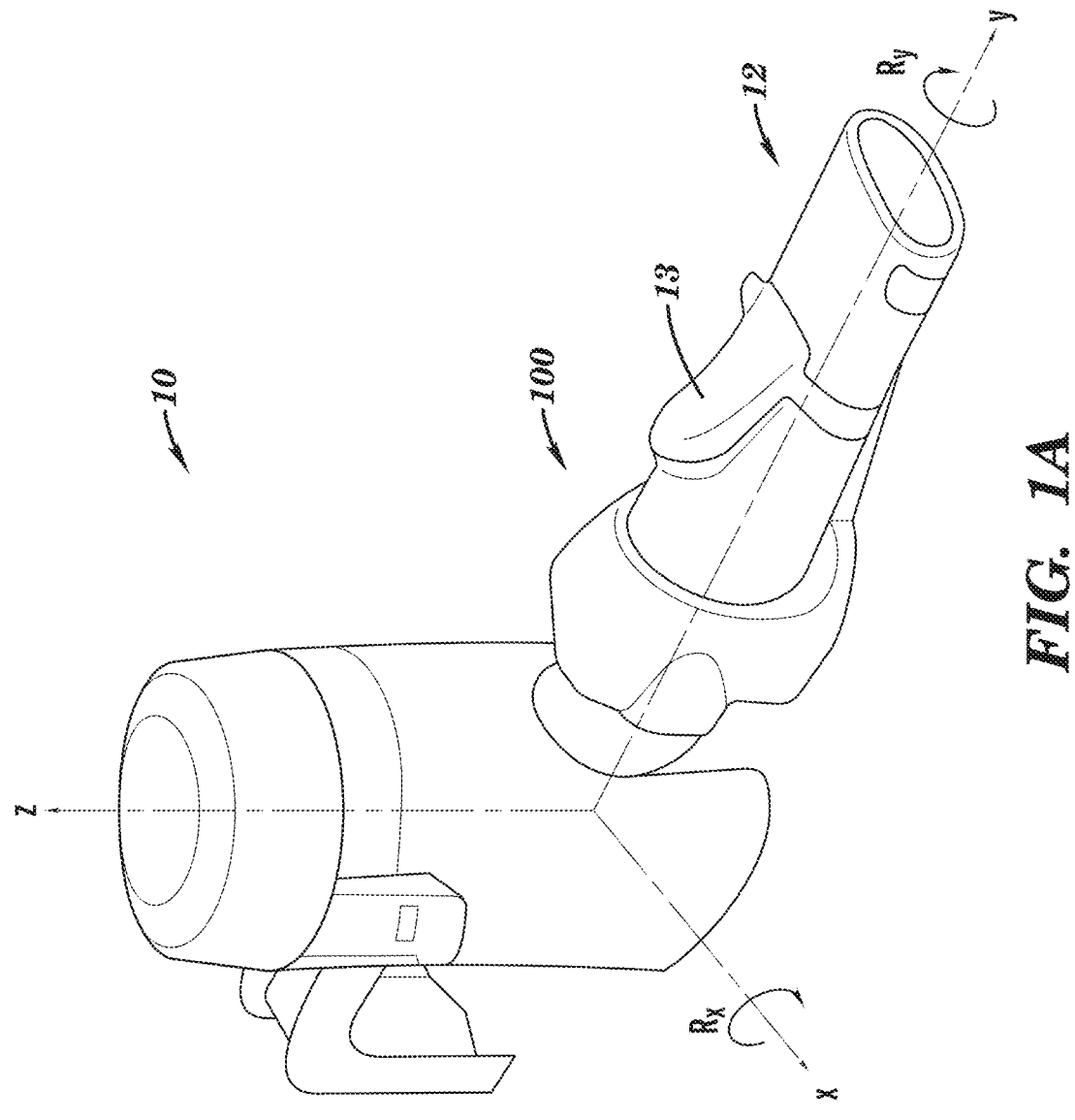
FIG. 1A shows a 3D projected view of a nebulizer monitoring device.

The present application is directed to methods and systems for the management of inhalation therapies. For example, the management of inhalation therapy can include detecting and recording adherence to inhalation treatment therapy regimens and monitoring and recording the dosages taken, the user's condition (e.g., temperature, respiratory rate, tidal volume) and the environmental conditions the user is exposed to (e.g., air quality). The treatments can include nebulizer therapy and monitoring thereof for the treatment of COPD or other respiratory diseases (e.g., asthma, cystic fibrosis) that are treated with nebulized therapies. Generally, the invention relates to devices, systems and methods for assisting users, care givers and health care providers with the management of therapies requiring nebulizer treatment. The same systems can also be used for monitoring a subject in a clinical study.

As used herein where context permits, the term "user" generally refers to a subject of a clinical study, a patient or a care provider who assists a subject or patient. For example, and without limitations a user can be a patient undergoing a nebulizer treatment by using a device as described herein, using a system as described herein, or monitoring the use of a device as described herein. Alternatively, without limitations, a user can be a subject in a clinical trial using the device as described herein as part of the trial, using the system as described herein as part of a clinical trial, or monitoring the use of the device as part of a clinical trial. Also, without limitations, a user can be a care provide (e.g., a spouse, relative, friend, nurse, and/or hired aid) who helps a patient or subject to use a device as described herein, who helps the patient or subject to use a system as described herein, or who helps the patient or subject monitor the use of the device. In some embodiments, the term user can refer to two or more patients, subject and/or care providers. For example, a user who is alerted by an indicator of a monitoring system should be understood to mean that both a care provider and a patient can be alerted by the monitoring system. In some embodiments a user can be both a patient and a subject, for example a patient who is undergoing an experimental treatment.

COPD is a disease that typically occurs in male and female patients≥40 years of age and is associated with a high disease burden including reduced quality of life, impaired functioning and significant direct and indirect costs. COPD patients can also have an acute exacerbation of the COPD symptoms, where inflammations can lead to narrowing and accumulation of mucus in airways. The exact cause of these exacerbations is not always known but in some cases can be due to viral and bacterial infections in the lungs and also from inhaling irritating substances from the environment like heavy air pollution or from pollen or other allergens. Early detection of an exacerbation is important because untreated these can often lead to protracted recovery, worsening of co-morbidities and death. Patients with COPD therefore require adequate education on the disease process, such as exacerbations and comorbidities, and also on the use of different medications and devices. Since the demography of COPD suffers includes a population often with other medical challenges requiring separate medication regimes and in some cases a reduced ability to self-regulate, compliance of an inhalation regime can be challenging. The correct use of devices and onset of an exacerbation is often done by self-reporting or observation by a healthcare provider or another person (e.g., spouse of care giver).

Nebulizers are drug delivery devices that are used to deliver a medication that is in the form of a solution or a suspension directly to the airways by aerosolizing the solution so that it can be inhaled by the user such that the medication is delivered directly to the tissues of the inflamed and/or irritated airway. Three common types of Nebulizers include a jet nebulizer, an ultrasonic nebulizer and a mesh nebulizer. These are designed to produce an aerosolized medication from a medical solution (e.g. or suspension) with particles between about 1 and 5 μm in diameter that can be inhaled and deposited in the airways of a user via a mouthpiece, nosepiece or facemask. Or through connection of the nebulizer to a mechanical ventilator system. Other particle size distributions can be used/targeted, but this is done with the understanding that particles between about 10-15 μm in size tend to deposit mostly in the upper air-ways, particles between about 5-10 μm size tend to reach the large bronchi, particles about 1-5 μm in size tend to penetrate to the lower airways and lung periphery, and smaller particles or vapor will mostly likely be inhaled and exhaled without deposition, although some deposition/condensation may occur.

In a jet nebulizer, the medical solution is added to a reservoir which is connected with a capillary tube on a first open end of the tube. A compressed gas source produces a stream of gas, e.g., a jet stream, which is projected through a small opening across a second open end of the capillary tube to draw liquid from the reservoir through the tube by the Venturi effect. Therefore, the gas (e.g., air) stream reduces the pressure at the second end of the tube, causing the liquid to be drawn from the reservoir through the first end of the tube and out of the second end. The liquid is aerosolized upon contact with the jet stream. The jet stream and aerosolized particles are directed through a chamber that can include baffles. The larger liquid particles contact and become trapped by the baffles such that the liquid from these particles can flow/drip back into the reservoir or another collection chamber. The baffles are generally designed to remove particles that are larger than about 5 μm in diameter. The smaller particles, e.g., <5 μm, remain aerosolized in the chamber and can exit the chamber through a port that is attached to a mouthpiece, nosepiece facemask, mechanical ventilator system, or a tube which is then connected to one of these. The mouthpiece is designed to be inserted into the user's mouth for intake of the aerosolized medication while the user inhales. For example, the mouthpiece can be designed to be inserted between the user's teeth and contacts/seals with the user's lips. A nose piece can have two tubes configured for insertion into nostrils, while a facemask can be placed over the mouth and/or nose for intake of the medication. The chamber can also include another opening, an air intake port, which allows ambient air to enter the chamber, for example, when the user inhales. Other ports, such as an exhale port on the mouthpiece or the facemask can also be included. Systems of one-way values can also be included to allow access of the aerosolized medication to the user via the mouthpiece/facemask and actuated, for example, when the user inhales, and directing/keeping the exhale out of the chamber. For example, one way values on the mouthpiece, air-intake, and exhale ports. In some systems, the air intake can be connected to an expandable chamber, such as a collection bag or expandable elastomeric ball, with can serve as a reservoir for aerosolized medication, e.g., contracting when the user inhales and expanding with new aerosolized medication when the user exhales, where the gas/air source is controlled by one way valves.

Ultrasonic nebulizers use high-frequency vibrations from a transducer (e.g., a piezoelectric material) that energizes the medication solution in the reservoir creating a standing wave that generates an aerosol in a chamber. The chamber can be connected to a mouthpiece such that when the user inhales, the aerosol is drawn into their lungs. The ultrasonic nebulizer can include one or more baffles to control the particle size (e.g., trap the larger aerosol particles) such that the ultrasonic nebulizer delivers an aerosol having less than about 5 μm particle size to the user. Ultrasonic nebulizers are generally more efficient than jet nebulizers and doses of a medications are appropriately adjusted to take this into account. For example, a 1 mL dose of a medication used with an ultrasonic nebulizer might require a 2 mL dose of the same medication when using a jet nebulizer.

Another common nebulizer is a mesh nebulizer or electronic nebulizer (eFlow nebulizer). Mesh nebulizers use electricity to vibrate a piezoelectric element connected to a fine mesh and contacted with a medicated solution to generate the aerosol. A key distinguishing feature of the mesh nebulizer as compared to the jet and ultrasonic nebulizers is that the diameter of the mesh determines the size of the particles, rather than baffles. Doses can also be more efficiently metered where the administration of small, set volume of drug in a 2-3 minute time window differentiates it from a jet nebulizer.

The devices described by the embodiments herein are universal and adaptable to use with any nebulizer, such as jet, ultrasonic and mesh nebulizers. In addition, the nebulizers can include a mouthpiece or a facemask. In some embodiments commercial nebulizers such as those available from PARI Respiratory Equipment, Inc, (e.g., Pari Trek S, Magnair®), VELOX, Philips Respironics (e.g., Respironics Sidestream©), Roscoe Medical (e.g., Roscoe Medical Portable Travel Nebulizer System, Roscoe Pediatric Nebulizers), Dynarex Corporation (e.g., Dynarex Portable Compressor Nebulizer), Meridian and Clinic Guard (e.g., ClinicalGuard® Ultrasonic Portable Neblizer).

As noted previously it is important in COPD management for patients to adhere to inhaled medications therapies and for early detection of exacerbations. It has been recognized herein that for treatments using nebulizers a monitoring system would greatly improve treatment compliance and exacerbation detection. Such monitoring systems and devices are described herein, for example where some embodiments of devices, methods and systems are shown by the figures.

In addition, a nebulizer monitoring system that collects physical data over time, such as the breathing rate, tidal volumes and temperature can be useful in monitoring a user (e.g., to monitor a disease progression) or for monitoring a subject during drug testing (e.g., during clinical trials).

The methods, systems and devices described herein can be used with any medication (e.g., bronchodilators, steroids, antibiotics) that can be nebulized by any nebulizer (e.g., the nebulizers described above). These medications can include for example, molecules and polymers (e.g., proteins) and often include a saline solution or other carrier media. Some specific examples include Long-Acting Beta-Agonist (LABA), Long-acting Muscarinic Antagonist (LAMA), Inhaled Corticosteroids (ICS), Short Acting Muscarinic Antagonist (SAMA), Short-Acting Beta Agonists (SABA), Budesonide, Azithromycin, Tobramycin, Pirfenidone and Revefenacin. Treatments can be for various lung diseases, for example, COPD, asthma, chronic bronchitis, emphysema, pulmonary fibrosis, cystic fibrosis and lung cancer. Since inhaled therapies also provide an entry into the blood stream, some embodiments for the methods, systems and devices described herein include drugs used with a nebulizer for systemic entry and treatment of non-lung related conditions.

Therefore, in accordance with some embodiments of the invention, the nebulizer sensing device 100 can be configured as a conduit that is connected between the source of aerosolized medication (e.g., a nebulizer) and to a mouthpiece, nosepiece or facemask. Sensors placed in the conduit can thereby detect the flows and flow rates and presence/absence of the medicated aerosol as the user inhales and exhales. FIG. 1A shows a 3D projected view of an embodiment including a nebulizer device 10, a nebulizer sensing device 100 and a mouthpiece 12. The figure also shows assigned x, y and z translational axis, and $R_x$ and $R_y$ rotational axis for the assembly. The nebulizer device 10 can include a medication reservoir for containing liquid medication, a nebulizer element (e.g., jet, ultrasonic or mesh, not shown) and a chamber for containing an aerosolized medication. The reservoir and chamber are not shown in this projection, for simplicity and are well understood components in the art. The chamber and reservoir can contain, for example, capillary tubes, baffles, piezoelectric elements (and electrical connections thereto), gas intake ports (e.g., connected to a pressurized gas source) and valves as previously described. In some embodiments the nebulizer device 10 can also serve as a holder, and, in these embodiments, the nebulizer device 10 can be configured to be held with appropriate handles, grips, groves and/or shape therefor. The nebulizer device 10 also includes a port or nebulizer mount 14 extending from the aerosol containing chamber. This port or nebulizer mount 14 can be connected via a first connector to a nebulizer sensing device 100. It is understood that in some alternate embodiments, conduits, such as a tube, can be inserted between the nebulizer device 10 and the nebulizer sensing device 100, where the conduit provides aerosol/air passage therethrough. The nebulizer sensing device 100 can also include a second connector that can engage/connect to a nebulizer mouthpiece 12 optionally including a flap valve 13 which opens upon exhalation and closes upon inhalation by the user using the device. The nebulizer sensing device 100 can include one or more sensors for detecting use of the nebulizer, and indicators for indicating the dosages taken, and/or the state of the user as described herein.

Figure 1B:
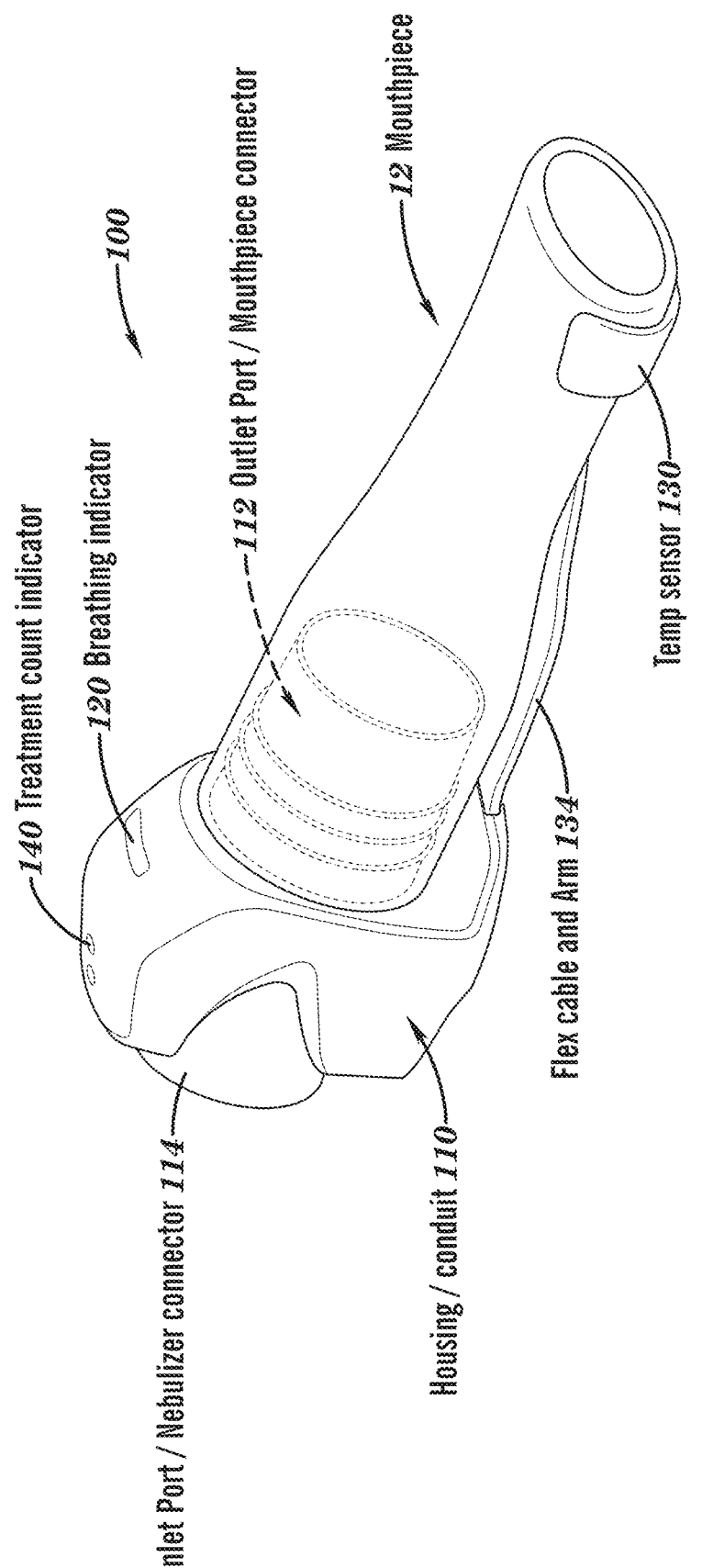
FIG. 1B shows a 3D projected view of a nebulizer monitoring device including some additional details.

The nebulizer sensor device 100 is shown in more detail by FIG. 1B which shows a 3D projection of the device. The device 100 can include a housing 110 forming a conduit between a first connector 114 (e.g., configured to engage and seal to a nebulizer mount 14) and an outlet port 112 adapted to engage and seal to the mouthpiece 12. The housing 110 can define a sealed path from the nebulizer mount 14 to the mouthpiece 12 such that gas inhaled via the mouthpiece 12 or exhaled via the mouthpiece does not escape through the conduit. The mouthpiece 12 is shown in a transparent view, although the mouthpiece can but need not be transparent. Therefore, the housing 110 is configured as a conduit for flow of aerosol/air through the connectors 114 and 112 in either direction, e.g., during user inhaling and exhaling. In some embodiments, as shown in FIG. 1A but not shown in FIG. 1B, the mouthpiece can include a one-way valve 13 which opens to the exterior environment upon exhaling and closes upon inhaling (e.g., it can remain closed when the device is not in use). In these embodiments the aerosol/air is exhaled through this one-way valve and does not pass back through connector 114. The housing 110 of the nebulizer sensor device 100 can also include one or more visual and/or audible indicators. In some embodiments the housing shows a treatment or dosage count indicator 140 and a breathing indicator 120. The breathing indicator 120 can be disposed, as shown, to be viewed by the user when the user engages the mouthpiece. The treatment count indicator 140 can be disposed, as shown, on the housing to be easily viewed before or after completion of the therapy.

Figures 2A, 2B:
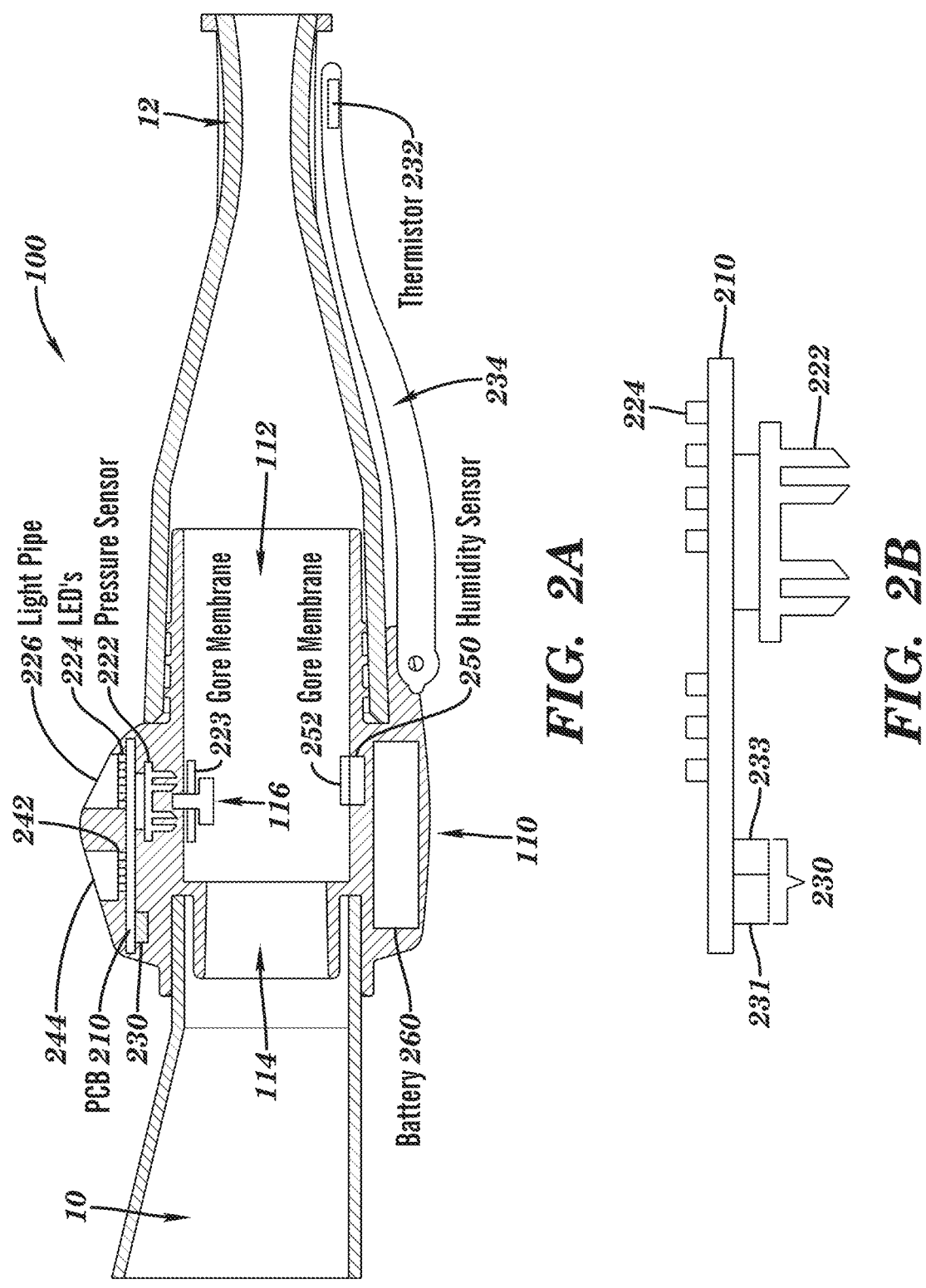
FIG. 2A shows a cross-cut plane view of a nebulizer monitoring device.
FIG. 2B shows a cross-cut plane view of a board of a nebulizer monitoring device including controlling components, sensors and indicators.

FIG. 2A shows a section view of the nebulizer monitoring device 100 according to some embodiments of the invention. As shown in the figure, the nebulizer mount 14 (e.g., a portion of the nebulizer device 10 that engages with first connector 114), is connected through first connector 114 to the housing 110, and the housing is connected to the mouthpiece 12 through outlet port 112. The components 14, 110 and 12 thereby define an internal conduit that allows the aerosol/air to flow from the nebulizer chamber to the mouthpiece 12. In some embodiments the housing 110, that includes an interior space or conduit as described and shown, includes one or more sensors disposed in the conduit such as a pressure sensor 222 and a humidity sensor 250. Protective elements such as protective membranes (e.g., Gore Membranes, available from W.L. Gore & Co.) 223 and 252 can also be provided to limit the aerosol liquids (e.g., that flow through the conduit) from accumulating on the sensors and affect their sensitivity. In some embodiments, the housing can include one or more indicators, such as a breathing indicator. For example, the breathing indicator can include one or more LEDs 224 and one or more light pipes 226 with one end proximate to the LEDs 224 to transmit light from the LEDs 224 to the external surface of the housing such that it can viewed by the user. In other embodiments the housing 110, can optionally or additionally include one or more other LEDs 242 and one or more light pipes 244 to convey dosage, usage or other information to the user. The housing 110 can also include a controller board such as a PCB board 210 with a controller 230 mounted thereto, as shown in the detailed view of FIG. 2B. The PCB 210 can include one or more accelerometers or gyroscopes 280 (e.g., for sensing motion and sending velocity and/or acceleration signals to the controller 230) and one or more wireless communication transceivers 290 (e.g., for transmitting and receiving data with external devices). The controller 230 can include a central processing unit (CPU) 231 and memory 233, for example, as part of an integrated circuit or system on a chip. The CPU 231 can also be connected to a timer unit and/or the timer can be included in the CPU (e.g., included as a hardware time or programmed as software time). The controller 230 can also include other integrated units for example for communication (e.g., transceiver 290) and power management (not shown). The controller 230 can include microcontrollers, e.g., wherein as used herein a "microcontroller" as used herein describes an integrated circuit designed to implement or control a specific operation in an embedded system and typically includes a processor, memory and input/output peripherals on a single chip. The controller 230 and/or the microcontroller can, for example, include an ARM based microcontroller, a PIC based microcontroller, or an Intel based CPU or microcontroller. The LED's, and sensors can be connected and in communication, e.g., electrically or wirelessly, with the controller. In some embodiments, as shown in FIG. 2A the LED's and pressure sensors are mounted/integrated on the PCB board and the humidity sensor is not mounted on the PCB board. It is understood that in some other embodiments, the various elements can be arranged differently, for example where the humidity sensor is mounted on the PCB board, the pressure sensor is not mounted on the PCB board or some/all of the LEDs are not directly mounted on the PCB board. In some embodiments, an internal (e.g., a battery or capacitor) and/or an external power source (e.g., conventional AC power adapter or power supply) can be used to supply power to the controller 230 and distributed as needed to power the various components. For example, power can be supplied through a connecting plug mounted on the housing 110 that connects to an external power supply (not shown) and/or through an internal or external battery 260 as shown. In some embodiments, replaceable batteries can be used. In some embodiments, the battery 260 can be a rechargeable battery, e.g., through direct electrical connection, for example, using a charging circuit or through induction, for example, using a wireless power transfer technology such as Qi or Near Field Communication (NFC).

In some embodiments, the pressure sensor 222 can include a differential pressure sensor or flow meter. Differential pressure flowmeters introduce a constriction in a pipe that creates a pressure drop across the constriction 116, in the direction of a flowing fluid/gas, and which can be measured using two pressure sensors 222, one on each side of the constriction. When the flow increases, more pressure drop is created as a fluid/gas flows through the constriction. Therefore, the differential pressure sensor can be calibrated for a specific material, such as air/aerosol to determine the speed (e.g., fluid flow rate) and the direction of flow through the pipe/conduit. For example, the upstream pressure sensor is expected to have a higher pressure than the downstream sensor and the sensor can be calibrated to determine the flow rate as a function of the upstream pressure and the downstream pressure. The controller 230 can determine the volume (e.g., tidal volume) of gas (e.g., air and/or aerosol) by associating a time stamp with each of the pressure measurements and flow rate value determined from the pressure measurements. For example, the volume of air and/or aerosol inhaled or exhaled can be determined as a function of the flow rate over a predefined time period. The direction of flow (e.g., inhale or exhale) can be determined by the position of the pressure sensors relative to each other and the mouthpiece 12 or the nebulizer device 10. For example, on inhale, the pressure at the pressure sensor nearest the nebulizer device 10 will generally be greater than the pressure at the pressure sensor nearest mouthpiece 12. For example, on exhale, the pressure at the pressure sensor nearest the nebulizer device 10 will generally be less than the pressure at the pressure sensor nearest mouthpiece 12. The controller 230 can record in memory the pressures, the flow rate and the time of each measurement to enable the controller 230 or a remote system to determine the tidal volume as breathing metrics such as how long each user inhales and exhales and how many breaths the user takes for each dose. The pressure, flow rate and time of each measurement can be transmitted to a remote system for further analysis.

In some embodiments, the device 100 can include a constriction made by a mesh or plate with one or more holes placed perpendicular to the flow in the conduit. In some embodiments the constriction can be minimized so as to minimize the amount of pressure drop and lessen the difficulty in breathing through the device for the user. The flow meter can include a time measurement element that can enable it to determine the flow rate directly. The flow meter can detect when flow starts and stops, e.g., by detecting when a pressure difference starts/stops and being coupled to the controller 230 and CPU 231 for data processing. It is understood that in some other embodiments, different flow meters can be used, for example, to replace or supplement the pressure sensor 222. For example, a mass flow meter can be used.

Figure 2C:
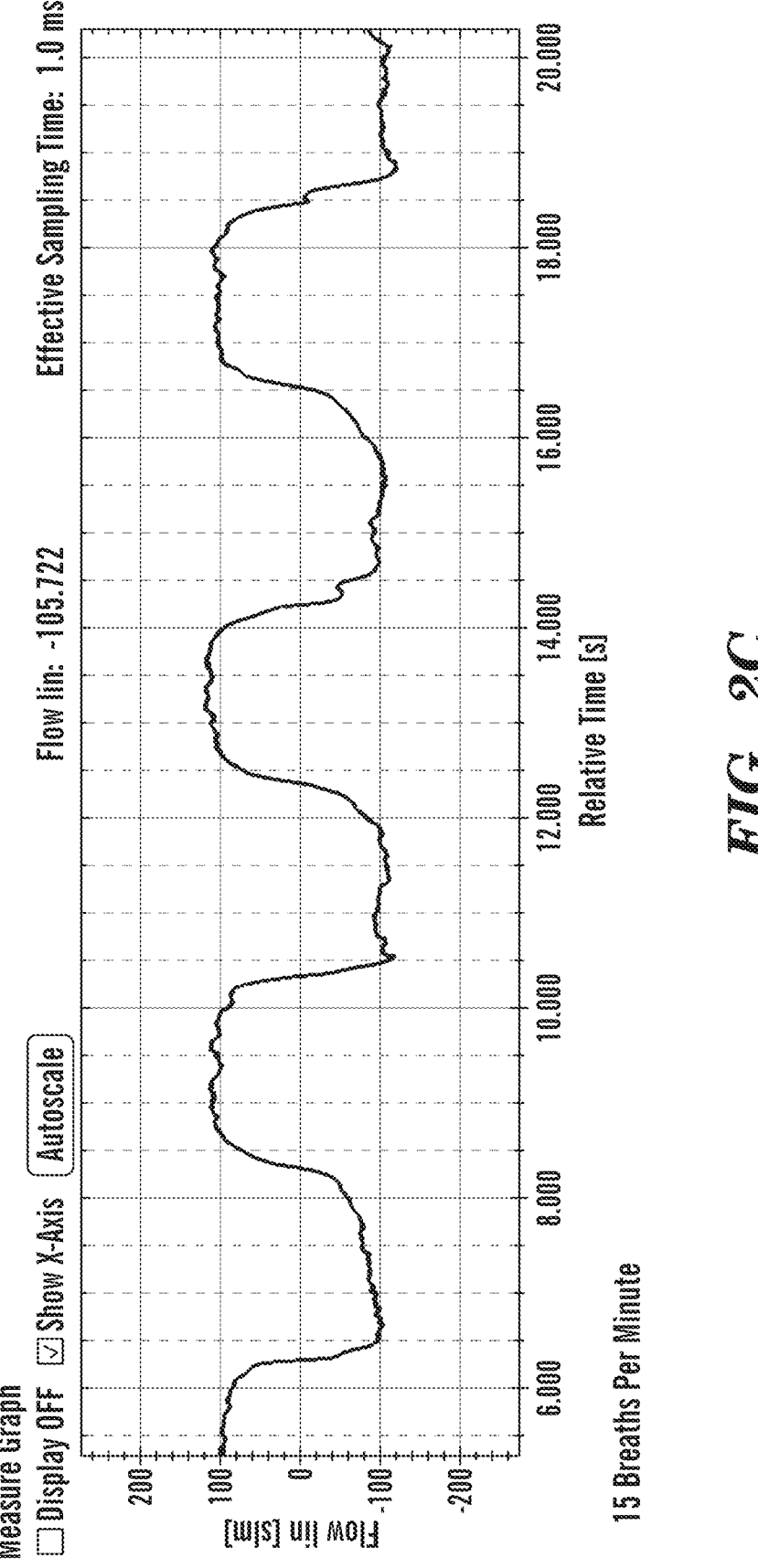
FIGS. 2C and 2D are two graphs showing plotted breathing data for two different breathing rates.
Figure 2D:
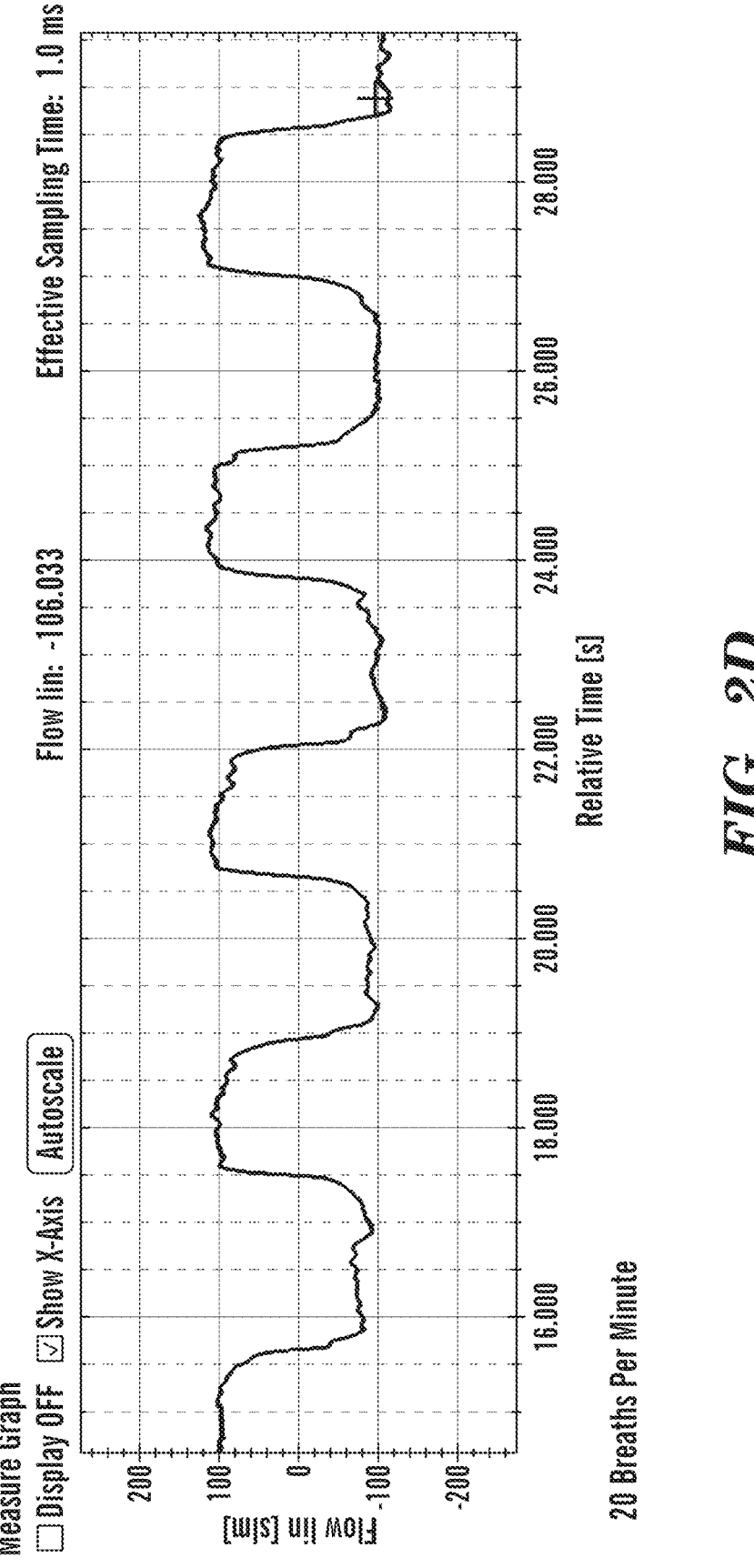

The flow rate measured combined with the amount of time during which flow is detected can be used to determine a total volume during the flow. FIGS. 2C and 2D show representative plotted breathing data as could be measured using the pressure sensor 222. FIG. 2C shows a respiration rate of 15 breaths per minute and FIG. 2D shows a respiration rate of 20 breaths per minute. The tidal volume can be calculated, for example, as the area under the inhalation curve.

Figure 3A:
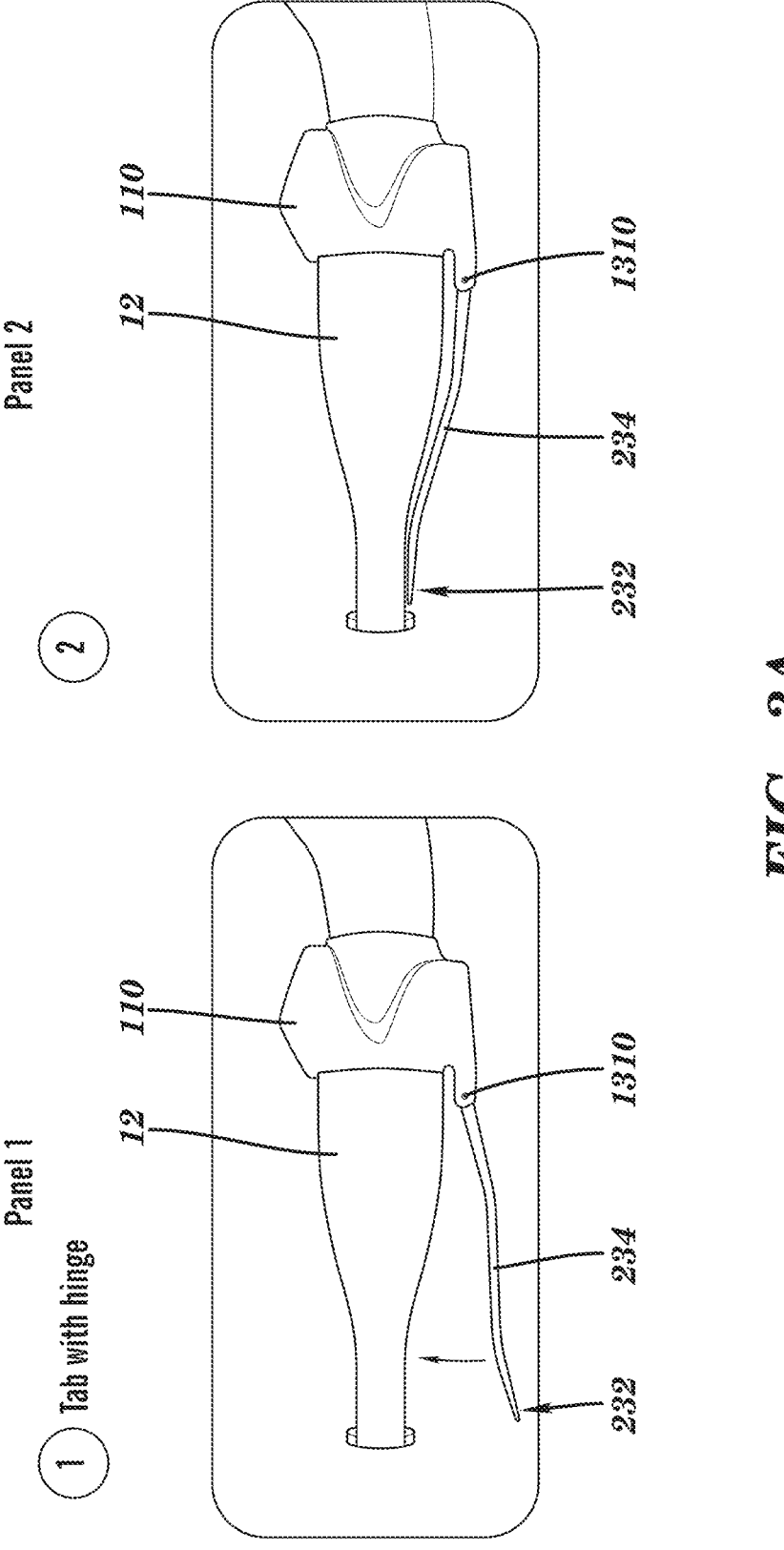
FIG. 3A, shows a tab and hinge configuration for positioning a thermistor near a mouthpiece for a nebulizer monitoring device.
Figure 3B:
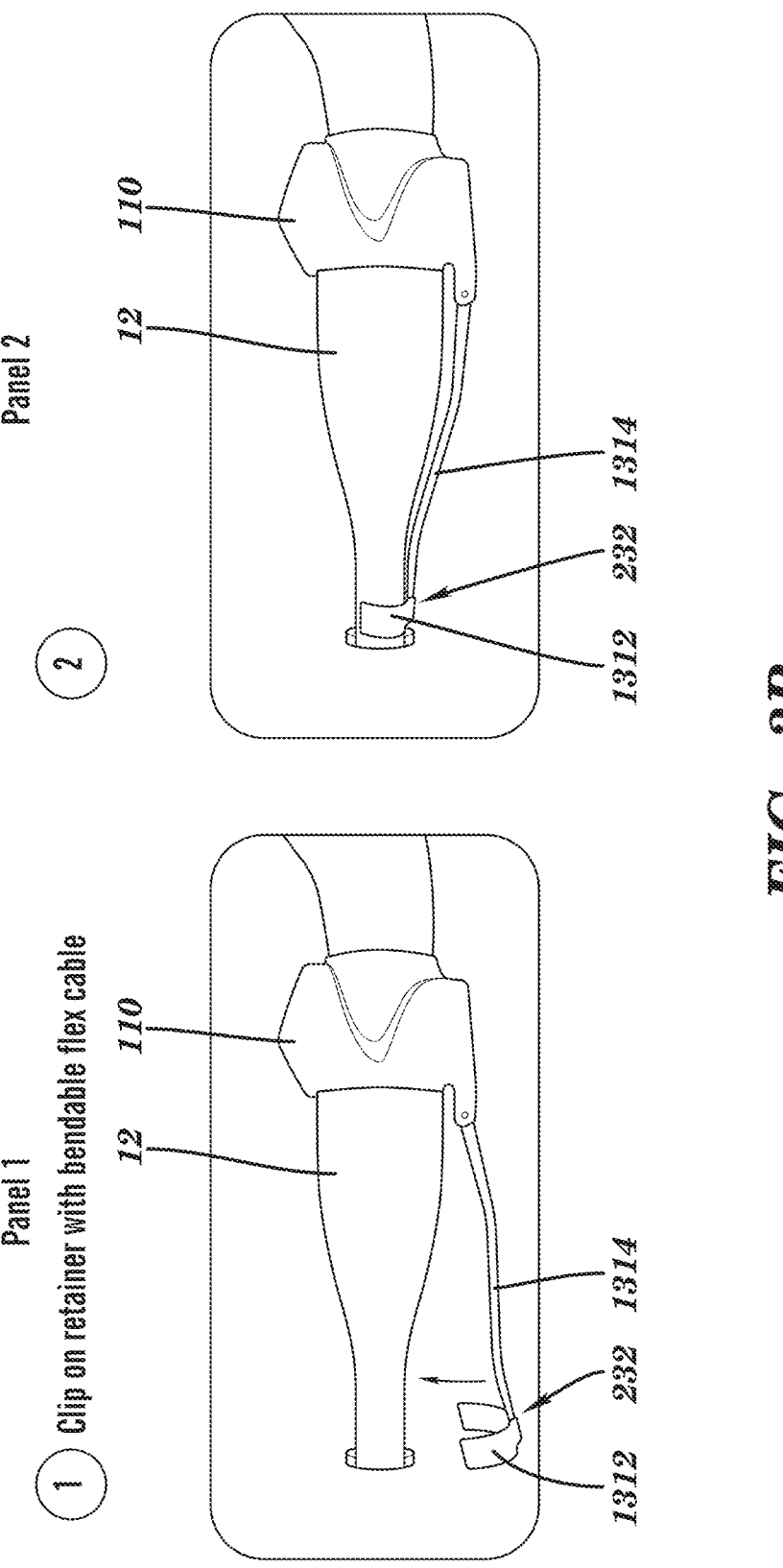
FIG. 3B shows a clip on retainer configuration for positioning a thermocouple near a mouthpiece for a nebulizer monitoring device.
Figure 3C:
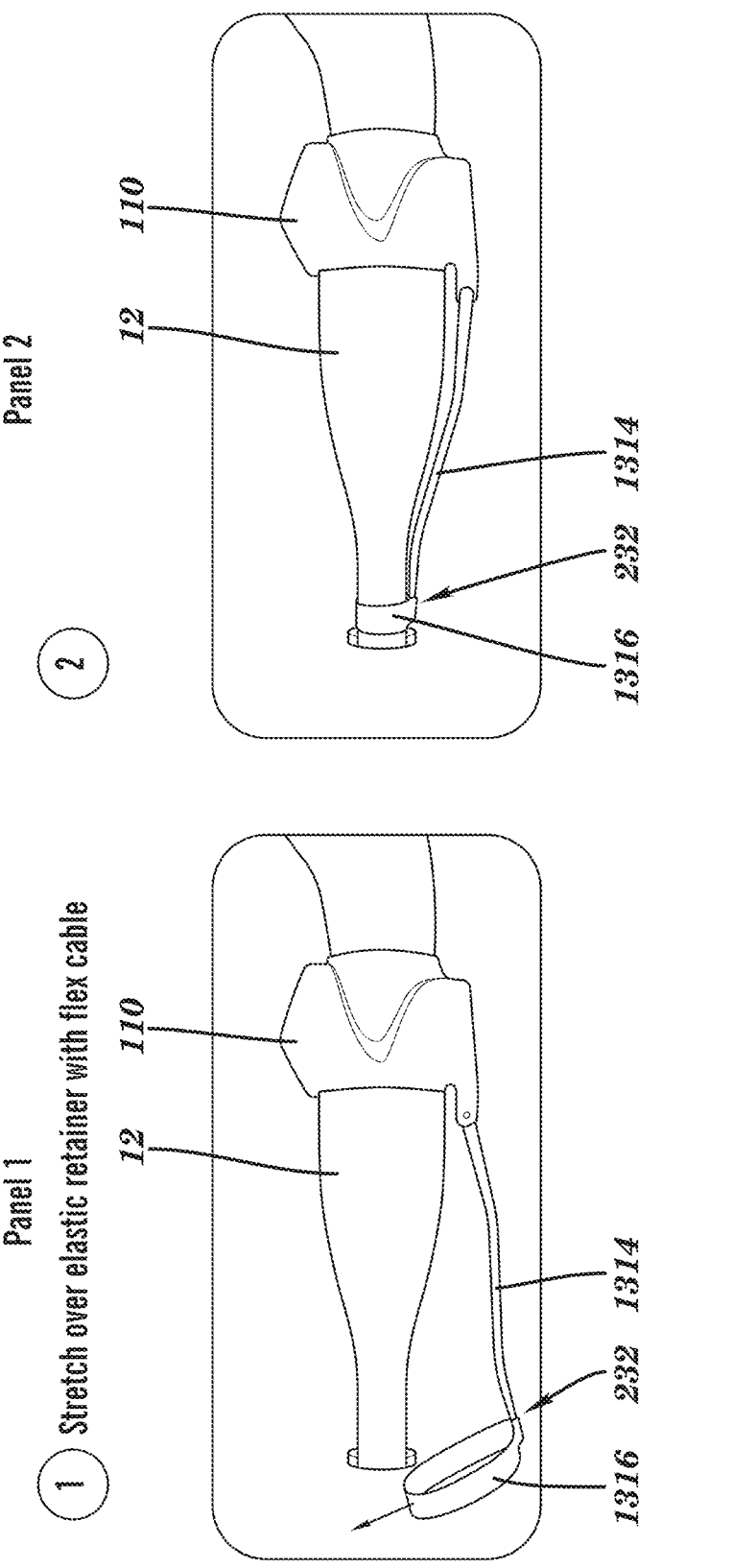
FIG. 3C shows a stretch over elastic retainer configuration for positioning a thermocouple near a mouthpiece for a nebulizer monitoring device.

In some embodiments, a nebulizer device, such as nebulizer device 100 can include one or more temperature sensors 232 configured to measure the temperature of the user using the nebulizer device. In some embodiments, the temperature sensor can be embedded in or positioned on the mouthpiece 12, such that when the user places their lips on the mouthpiece 12, the temperature sensor measures the temperature of at least one of the lips of the user. For example, the temperature sensor can include a thermistor or thermocouple connected to the controller 230, e.g., via an electrical cable/contact. In some embodiments, the nebulizer device 100 includes a thermistor 232 that is disposed at the proximal end of the mouthpiece 12 and an arm 234 can be used to electrically connect the thermistor 232 to the controller 230. FIGS. 3A, 3B and 3C show some embodiments for connecting a temperature sensor 232 to a proximal end of the mouthpiece 12, such that the temperature can become in contact with a user's lips during use. FIG. 3A, shows an arm and hinge configuration and includes a rigid arm element 234 and a hinge element 1310 and the thermistor 232 can be positioned in or on the arm element 234 at the end opposite to the hinge element 1310. FIG. 3A panel 1 shows the arm positioned when the device is not in use, while FIG. 3A panel 2 shows the arm 234 moved into position for the user to use, where the thermistor 232 is positioned near the proximal end of mouthpiece 12. FIG. 3B shows another optional embodiment, including a clip on retaining element 1312 connected to the controller 230 by a bendable and/or flexible cable 1314. FIG. 3B panel 1 shows the clip 1312 and cable 1314 in a position when the device is not in use, while FIG. 3B panel 2 shows the clip 1312 fastened to the mouthpiece 12 whereby the thermistor 232 is positioned against the proximal end of the mouthpiece 12 such that it comes in contact with one or more of the user's lips during use. FIG. 3C shows an embodiment using a stretch over elastic retainer 1316 with a flex cable 1314. FIG. 3C panel 1 shows the elastic retainer 1316 and cable 1314 in a position when the device is not in use, while FIG. 3C panel 2 shows the elastic retainer 1316 positioned on the proximal end of the mouthpiece 12, whereby the thermistor

232 position one the proximal end of the mouthpiece such that it comes in contact with one or more of the user's lips during use. It is noted that in FIGS. 3A-3C, the thermistor is not shown, rather the region where the thermistor resides is indicated by the arrow.

The humidity sensor 250 can be any humidity sensor know in the art. As used herein "humidity" refers to the water vapor content in air or other gases. Humidity measurements can be stated in a variety of terms and units. The three commonly used terms are absolute humidity, dew point, and relative humidity (RH). As used herein the "absolute humidity" is the ratio of the mass of water vapor to the volume of air or gas. It can be expressed in grams per cubic meter or grains per cubic foot (1 grain=$\frac{1}{7000}$ lb.) The "dew point" as used herein is the temperature and pressure at which a gas begins to condense into a liquid and is expressed in ° C. or ° F. As used herein the "relative humidity" or "RH" or "% RH" refers to the ratio (stated as a percent) of the moisture content of air compared to the saturated moisture level at the same temperature and pressure. In some embodiments the humidity sensor 250 is capacitive humidity sensor. For example, capacitive RH sensors consisting of a substrate (e.g., glass, ceramic, or silicon) on which a thin film of polymer or metal oxide is deposited between two conductive electrodes. In these sensors the sensing surface is typically coated with a porous metal electrode to protect it from contamination and exposure to condensation. In some other embodiments the humidity sensor 250 is a resistive humidity sensor which measure the change in electrical impedance of a hygroscopic medium such as a conductive polymer, salt, or treated substrate. For example, consisting of electrodes (e.g., noble metal electrodes) on a suitable substrate coated with a conductive polymer (e.g., polyimide), a salt, or an activating chemical. The changes in relative humidity are denoted by a corresponding change in the coating material's electrical resistance profile. Other humidity sensors known in the art can also be used in the embodiments of devices for monitoring nebulizer use.

In accordance with some of the embodiments of the invention, the sensors (e.g., pressure sensors 222 and humidity sensors 250) can include a protective element such as a hydrophobic breathable membrane covering sensitive elements of the sensor. As used herein, a hydrophobic breathable membrane is a structure, such as a film or sheet material, that will allow gases, such as oxygen, nitrogen, and water vapor to pass through but will not allow larger materials through, such as liquid or solid particulates. For example, the hydrophobic breathable membrane will not allow anything larger than about 10 nm to pass there through (e.g., larger than about 100 nm, larger than about 0.5 μm) In some embodiments the hydrophobic breathable membrane is Gore membrane 252 and 223. The hydrophobic breathable membrane ensures, or minimizes, the deposition of any large particulates, such as liquid particulates in the aerosol, on sensitive parts of the sensors. These types of membranes can be used prevent or reduce fouling and/or corrosion and minimizes anomalous or incorrect readings and damage to the sensors.

It is understood that other embodiments of the nebulizer monitoring device 100 can include other sensors such as a temperature sensor or $CO_2$ sensor in the interior space (conduit) of the housing 110. In addition, it is understood the placement of the sensors is a matter of choice of the practitioner, for example, the sensor can be positioned one or adjacent to the inner surface of the conduit or it can be suspended or positioned away from the inner surface of the conduit. For example, the placement of any given sensor can be determined based on its mode of operation and the characteristic it is intended to measure.

In some embodiments the housing can include an accelerometer and/or gyroscope 280, and configured to measure movement and position of the nebulizer device 100 during use. For example, the accelerometer and/or gyroscope 280 can be used to detect when the nebulizer device 100 is picked up, to initiate the monitoring function, and to measure its orientation during use.

In some embodiments, the accelerometer 280 can be used to determine if the device is being used in the correct orientation. As used herein, the correct orientation is an orientation where the nebulizer can function so that all or most (e.g., more than about 99%, more than about 95%, more than about 90%, or more than about 80%) of the medical solution in the nebulizer reservoir is nebulized and not lost, for example due to spillage from the reservoir when the nebulizer device 100 is tipped on its side during use. In accordance with some embodiments of the invention, each nebulizer device can be designed to operate in an optimal orientation or orientation range (e.g., within 10 degrees of horizontal. For example, for nebulizers such as those shown by FIG IA, the correct orientation is to have the mouthpiece horizontal to the ground and without any tilt angle, e.g., where the plane defined by the xy translational axis shown in the figure is parallel to the ground. For this orientation the Rx and Ry rotational axis can be defined as having an angle of zero. In some embodiments the correct orientation is where the angles of Rx and Ry are between about –5 and +5 degrees (e.g., between about –10 and about +10 degrees, between about –15 and about +15 degrees, or between about –20 and about +20 degrees). As an alternative description, accelerometer data can detect a gravity vector data and can be used to detect an angle with respect to the horizontal/vertical of the device. Therefore, the accelerometer 280 can measure the orientation of the device 100 and by way of the controller 230 can store this information in memory and transmit this information to the remote system.

The accelerometer 280 can also be used to "wake up" the device from a "sleep" when the monitoring device 100 is picked up. As used herein the device is in a "sleep" or "sleep mode" when at least some of the elements of the device, such as some of the sensors are off and receive no power or a level of power below a threshold needed for them to operate as sensing devices. There may be, in sleep mode, power supplied as needed to maintain a sensor but the sleeping sensor does not collect data or send signals of collected data to controller 230. In some embodiments, in a sleep mode, the accelerometer 280 is connected to the controller 230 and receives power from and communicates with the controller, while other sensors receive little or no power. For example, the controller 230 can operate in a mode of operation wherein the controller 230 continually monitors signals from the accelerometer/gyroscope 280 and through a software algorithm run by CPU 231 determines if the device 100 has been picked up (e.g., the algorithm determines that motion (e.g., velocity and/or acceleration over time) of the accelerometer or gyroscope 280 is greater than a predefined threshold value for more than a short period of time. For example, if the accelerometer/gyroscope 280 detects an acceleration and/or a velocity that exceeds a predefined threshold value for a period of time, such as at least about 3 seconds, the algorithm can determine that the device has been picked up by a user. The pre-determined time can be selected such that the device will not wake up due to an accidental movement e.g., due to bumping a nightstand upon which the device is resting. In some implementations, the nebulizer monitoring device 100, using accelerometer data and a software algorithm run by CPU 231, can detect movements that are not associated with being picked up or accidental movements, for example, movements caused in an airplane or the rocking motions in a ship. If the algorithm determines the device has been picked up by a user, the controller can be programmed to execute instructions to "wake up" the nebulizer monitoring device 100, placing it in normal operating mode. As used herein, the device is in a wake up or operating mode, or is "woken up" to a state where the device is executing the software instructions or program that can be used to monitor the use of a nebulizer, such as turning on power to one or more of the sensors such as the pressure sensor 222 and humidity sensor 250, and the indicator LEDs 224 and 242 (e.g., to indicate that the device is operating to the user), and associated components on controller 230 so that flow and humidity data can be collected. Optionally the process of waking up the nebulizer monitoring device 100 can include a powering up routine, executed by the controller 230 to turn on and check that each element is connected to the controller 230 and is functioning properly. Optionally, the process of waking up can occur in stages such as first monitoring signals from one or more of the pressure or humidity sensors and processing the received signals to determine if the nebulizer device 10 is being used by a user. For example, the time between moving the device 100 and using it can vary, e.g., in some embodiments some assembly is required before the device is used with a nebulizer, as will be described in more detail below, and therefore the device need not be fully awake immediately. By fully awake, it is meant that at least one, and in some embodiments all, of the sensors of the device are on and monitoring for a dosage delivery, and for the end of the dosage delivery. The end of the dosage delivery can be due to a drop in humidity sensed and/or cessation of inhalation/exhalation as detected by a flow sensor as discussed herein. In some embodiments the "sleep" mode includes data transfer, as will be described below. In accordance with some embodiments of the invention, after the device 100 is woken up or enters wake mode, the controller 230 can start a timer for 5, 10, 15, 20, 25 or 30 minutes and at the expiration of the timer, the controller 230 can return the device 100 to sleep mode.

Prior to use of the nebulizer monitoring device 100, a medicated solution is added to a reservoir in the nebulizer device 10. The medicated solution can be in a dosage form such as a cartridge or package where the nebulizer device 10 is configured to accept and pierce or open a portion of the cartridge or package. The medicated solution can then drip or flow into the reservoir. In some configurations, the cartridge or package can function as the reservoir, e.g., wherein piercing or opening the cartridge or package connects the contents to a capillary tube used in a jet nebulizer configuration. In some embodiments, the cartridge or package can contain an amount of medicated solution used as a single dose for one treatment session. The time to take a dose and amount of liquid for the dose depends on the treatment and on the type of nebulization device. For example, nebulization cycle times are different, whereas a jet nebulizer takes longer to administer a nebulized therapy than an ultrasonic nebulizer and may require more medicated solution to dispense a therapeutically effective dose of a nebulized medicine. In some embodiments a proper dose takes between 2-20 min (e.g., 2-3 minutes, 3-7 min, 5-12) to be correctly taken.

Also prior to using, the nebulizer is assembled, either by the user. The nebulizer device 10, the nebulizer sensing device 100, and the mouthpiece 12 can be inspected e.g., to ensure they are clean, prior to being assembled. Other components of the nebulization system, as may be needed, can also be assembled or connected, for example any power supply or tubing can be connected/switched on if needed. As described above, in some embodiments, the device 100 is woken up automatically by motion that can be sensed by an accelerometer 280 and accelerometer signals received by the controller 230. In addition to assembly, in embodiments, the temperature sensor 232 can be moved into operating position such that the temperature sensor 232 is in position close to the mouthpiece 12. In some embodiments an indicator element, e.g., mounted to the housing 110, will indicate by lighting, vibration or sound emission that the device is powered up and optionally to indicate it is ready to use. (i.e., properly assembled). For example, such indicators can be actuated by electrical or inductive contacts and switches between the members 10, 100, 12 all connected to the controller 230. Also, as previously described, in some embodiments using an accelerometer 280 in or on the housing 110, handling the device 100 such as during assembly, will cause the device to wake up so that the sensors will turn on based on a predefined software algorithm or program. The motion signals detected by the accelerometer 280 can be used by a software program executed by the controller 230 to determine whether the device is assembled correctly. This software algorithm can use machine learning to detect and learn the motion associated with correct device 100 assembly. For example, the machine learning algorithm can receive as inputs, a sequence of motion signals and determine how closely the sequence of motion signals matches one or more learned acceptable assembly sequences, in order generate a measure of correctness for device assembly and, optionally, trigger an indicator to indicate visually (e.g., a green light for correct when the measure of correctness is above or below a predefined threshold and red light for incorrect when the measure of correctness is below or above a predefined threshold).

After proper assembly, the user inserts the mouthpiece into their mouth, for example between the teeth. In embodiments where a facemask is used, the facemask is appropriately placed. These embodiments where a facemask is used, the facemask can include a temperature sensor positioned for insertion into or contact with a user's mouth or a temperature sensor located on the facemask to come in contact with the user's face to measure their temperature. For the embodiments including a temperature sensor, such as 232, this temperature sensor is contacted with at least a portion of the lip, for example contacting the lower lip where 232 can be set in the mouth but not past the user's teeth/gums. The thermistor signal or data is sent to the controller 230 for storage in memory, processing (e.g., to convert the signal to temperature) and optionally, for transmission to a remote system. In some embodiments, the thermistor signal is measured as resistance which can be translated by a software program executed by the controller to a lip temperature, and further translated to a core temperature (e.g., by known or measured/calculated correlation of lip to core temperature in a user). Therefore, by use of temperature sensor 232, temperature data of the user can be measure and tracked when administering a treatment. Such information is useful in determining the general health of the user, such as early detection of an exacerbating condition that lead to elevated body temperatures. Temperature monitoring can also serve as one indicator of compliance since proper and consistent placement of the sensor in the user's mouth will lead to temperature sensing consistent with a user's body temperature, while improper use may lead to no or erratic temperature readings. As previously described, in some embodiments a temperature sensor is included, in the conduit of the interior space or conduit of housing 110. The temperature sensor in the conduit can record breath temperature which, through art know correlations, relates to core temperature of the breathing user. The conduit temperature sensor can be a redundant temperature sensor to 232 or can provide an alternate temperature sensor instead of sensor 232.

Continuing from above regarding the user's use of the nebulizer monitoring system 100, after proper insertion of mouthpiece 12 into the mouth, the user is directed or instructed to breathe (e.g., inhale and exhale), for example using slow deep breaths, or tidal breathing. In some embodiments, the flow sensors (e.g., pressure sensor 222) are engaged prior to enabling nebulization/aerosolizing of the medicated solution. In these embodiments, the flow sensors send signals or data of a user's inhaling and exhaling of ambient air to the controller 230 and from these signals or data, the controller 230 can execute a software program that determines the volume of inhaling and exhaling and tidal volume for the treatment session. For example, the data can be sent to a remote system (e.g., an external computer or a cloud based computer system) and the data can be analyzed using software programs executed on the remote system to determine a measure of tidal volume for the user during each treatment session. In some embodiments, the nebulizing elements (e.g., jet nebulizer, piezo nebulizer, mesh nebulizer) will be enabled once proper breathing has been established and the user can begin the therapy by inhaling the dose of the medication. In addition to temperature, the tidal volume and respiration rate can also be used for monitoring the user and where the tidal volume and/or respiration rate is outside of a normal range for the user, this can be used to indicate to the user or a care giver of an onset of an exacerbation condition. For example, where a smaller tidal volume is measured as compared to the user's normal or baseline tidal volume (e.g., a previously determined mean, average or threshold tidal volume value), controller 230 or the remote system can communicate a signal indicating that the potential for an exacerbating condition has been detected. And, for example, where a faster or slower respiration rate as compared to the user's normal or baseline respiration (e.g., a previously determined mean, average or threshold respiration rate value), controller 230 or the remote system can communicate a signal indicating that the potential for an exacerbating condition has been detected. In some embodiments, the measure tidal volume or respiration rates of the user, in addition to being stored in memory by the controller 230, can also be communicated in real time to the user by indicators such as LED lights 224 or wirelessly to a smart phone, remote computer or base station.

FIGS. 4A-4B and FIGS. 5A-5B show how LED lights 224 can be arranged and operated under the control of the controller 230 to provide communication and feedback to the user both in real time during use and afterward to keep track of use and dosage.

Figure 4A:
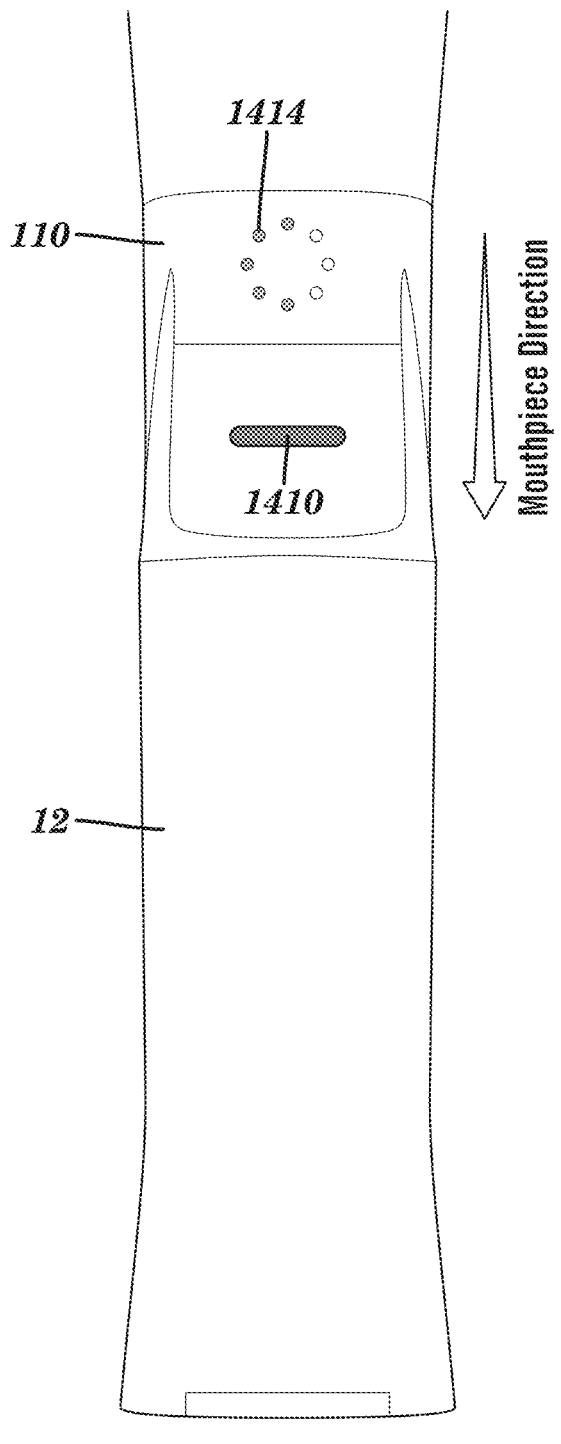
FIG. 4A is a top down view of an embodiment showing a mouthpiece and a housing of a nebulizer monitoring device.
Figure 4B:
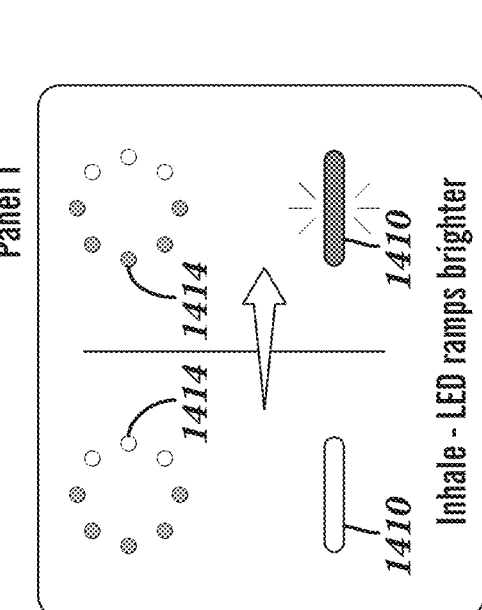
FIG. 4B shows pictorially how in some embodiments an intensity of a light can be used as an indicator of intensity of inhaling and exhaling.

FIG. 4A shows a top view of some embodiments showing the mouthpiece 12 and housing 110. In this configuration, the indicator 1410 has a shape, elongated in a direction perpendicular to the axis of flow of medicament in the mouthpiece, where the LED lights 224 and light pipe 226 provide an increase or decrease of light intensity of the indicator. FIG. 4B shows how the intensity of the light can be used as an indicator of intensity of inhaling and exhaling. For example, controller 230 connected to the pressure sensor 222, can establish the flow direction and flow rate and using an algorithm as part of a software program executed by the CPU 231 and convert this to appropriate currents/voltages to modulate the intensity of light emitted by LEDs 224. FIG. 4B panel 1 shows an embodiment where the intensity of light from indicator 1410 increases when the user inhales. FIG. 4B panel 2 shows an embodiment where the intensity from the indicator decreases when the user exhales. The intensity of the light can indicate the direction of flow as well as amount of flow, thereby providing real time information to the user regarding use of the nebulizer. For example, the user will have a real time indication as to whether or not they are breathing tidally or taking deep enough breaths for effective treatment.

Figure 5A:
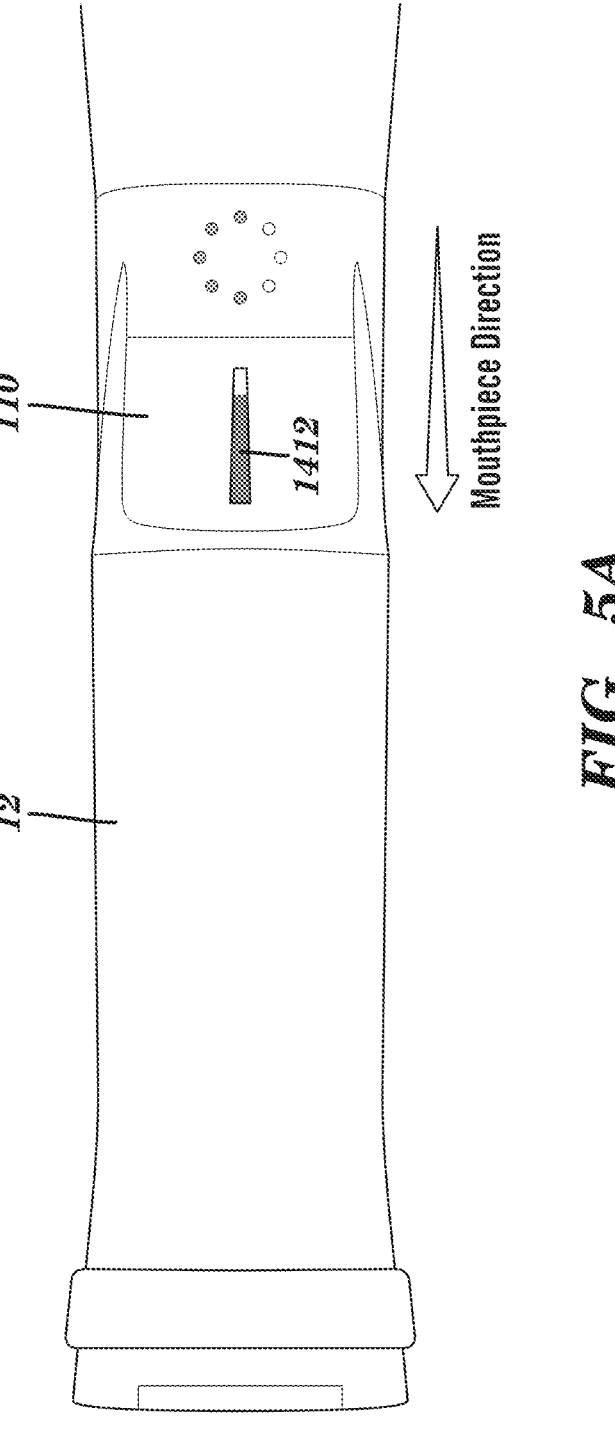
FIG. 5A is a top down view of an embodiment showing a mouthpiece and housing of a nebulizer monitoring device.
Figure 5B:
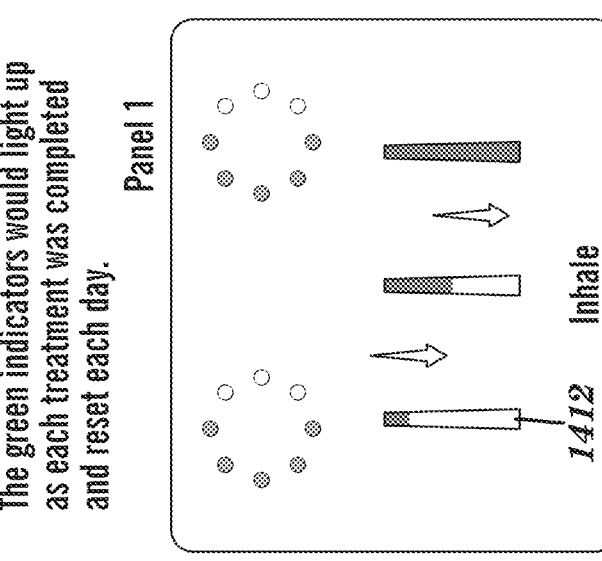
FIG. 5B panel 1 and 5B panel 2 show an embodiment where elongation within the confines of an indicator shows a user is inhaling (FIG. 5B Panel 1), and contraction within the confines of indicator shows that the user is exhaling (FIG. 5B Panel 2).

FIG. 5A is a top view of some other embodiment showing the mouthpiece 12 and housing 110. In this configuration, the indicator 1412 has a shape, elongated in a direction parallel to the axis of flow of medicament in the mouthpiece. In this embodiment, the LED lights 224 and light pipe 226 can provide the effect or impression of elongation or growth within the confines of indicator 1412. FIG. 5B panel 1 show the elongation within the confines of indicator 1412 as the user inhales. FIG. 5B panel 2 shows a contraction within the confines of indicator 1412 as the user exhales. The elongation and contraction can be produced, for example, by a series of LED lights that light up successively according to a software program executed by controller 230 in response to signal received from the pressure sensor 222. The elongation/contraction can provide a real time indication to the user as to their breathing through the nebulizer to receive their dose of medication.

Figure 5C:
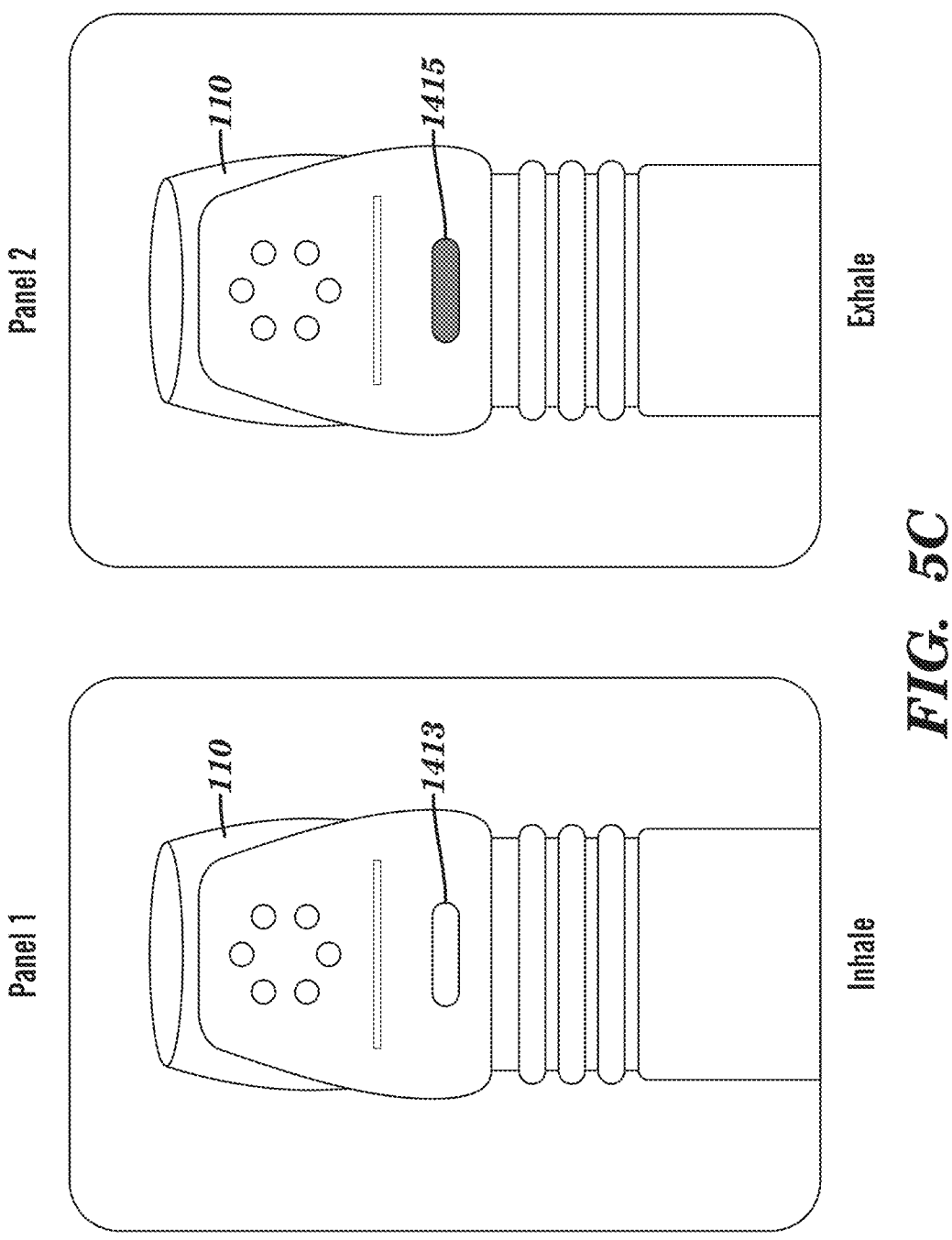
FIG. 5C shows a top down view of a housing of a nebulizer monitoring device having different color lights as indicators.

In some embodiments different frequency (color) lights can be used to indicate, for example, inhaling and exhaling. For example, FIG. 5C shows a top view of a housing 110 having different color light 1413 and 1415 emitted from the indicator. FIG. 5C panel 1 shows a blue light emission 1413 from the indicator indicating an inhale, while FIG. 5C panel 2 show the indicator emitting a purple light 1415 during an exhale. The intensity (or brightness) of the light (in each color) can be controlled by the controller 230 and used to indicate in real time, the air flow rate of the inhalation or exhalation.

In accordance with some embodiments of the invention, only the inhalation portion of a breath is monitored. For example, embodiments that include the valve 13 (FIG. 1A) since in this embodiment the flow sensor as described herein would only sense inhalation as an exhalation breath would not cause flow past the pressure sensors 222 (FIG. 2A). In some embodiments, a valve such as 13 could be included in a configuration with the device so that the exhalation would be detected. For example, the valve 13 could be placed between pressure sensor 222 and nebulizer device 10, either as part of the nebulizer monitoring device 100 or as part of the nebulizer device 10.

It is understood that some other embodiments can use other indicators to communicate inhaling and exhaling intensities. For example, some embodiments can alternatively or additionally include audible indicators that emit loud or soft sounds, beeping, a chord or musical fragment to indicate the flow of air/aerosol in the device 100. Also, audible indicators can make sounds that change in frequency and/or amplitude (e.g., loudness) depending on breathing intensity and/or direction (e.g., inhale vs exhale). Some other optional embodiments can include vibrating members, for example, that can change vibration intensities based on flow direction or rate of air/aerosol in device 100.

During the treatment session, the use of the nebulizer can be monitor by the nebulizer monitoring device to record information regarding the treatment session, for example using memory element 234. In addition to inhalation and exhalation data as describe above, dose data (e.g., an inhalation wherein the humidity sensor indicates that the humidity of the inhaled air is greater than a predefined threshold) can be recorded. The controller 230 can include a timer and a real time clock (e.g., either in hardware or software) that records the date and time and stores the start date and time (e.g., when the first inhalation is recorded) and stop data and time (e.g., when the last inhalation or exhalation is recorded) of each treatment session. Each inhalation and exhalation can be recorded as set of data points indicating an air flow rate (or pressures from the pressure sensors) and optionally an air flow direction, along with a date and time of the recording or a time offset from a predefined date and time.

In some embodiments the nebulizer monitoring device 100 can use flow data to determine if a dose has been taken and completed and then shut the nebulizer monitoring device 100 down. For example, the CPU 231 can be programmed to shut the device off or go into sleep mode after a predetermined time e.g., the prescribed time for a dose of the medication such as 5-20 min (e.g., 2-3 min, 3-7 min, 5-12 min) and/or the device is not moved (e.g., no change in accelerometer signal) for a predefined period of time (e.g., 5 min, 10 min, 15 min, 20 min, 30 min). The device 100 can alternatively or additionally be programmed to shut down or go into sleep mode when the controller 230 (via the pressure sensors 222) does not detect flow (e.g., no pressure or flow signal or no change in pressure or flow signal) for 10 or more seconds (e.g., 20 s or more, 30 s or more, 60 s or more, 5 min. or more) after the device 100 is awakened and/or not moved (e.g., no change in accelerometer signal) for a predefined period of time (e.g., 5 min, 10 min, 15 min, 20 min, 30 min). In some embodiments, the nebulizer monitoring device 100 can be programmed to shut down or go into sleep mode when the controller 230 (via the pressure sensors 222) does not detect a change in flow that crosses zero (e.g., see FIG. 2C or 2D) for more than 10 seconds (e.g., 20 s or more, 30 s or more, 60 s or more, 5 min. or more), indicating that inhalation and exhalation through the device has stopped. In some embodiments, the controller 230 can determine if a dose has been taken by processing the amount of time during which inhalation/exhalation flows have been detected and comparing the time duration to the prescribed threshold for administrating the dose. For example, a dose can be considered completed if the time of inhalation and exhalation measured by the nebulizer monitoring device 100 is at least 80% of the prescribed time. For example, if the prescribed time is 2-3 min, a dose is considered taken if the nebulizer monitoring device 100 recorded inhalation and/or exhalation for at least 1.6 min, while if the prescribed time is 5-12 min, a dose is considered taken if the device 100 recorded inhalation/exhalation for at least 4 min.

Figure 6:
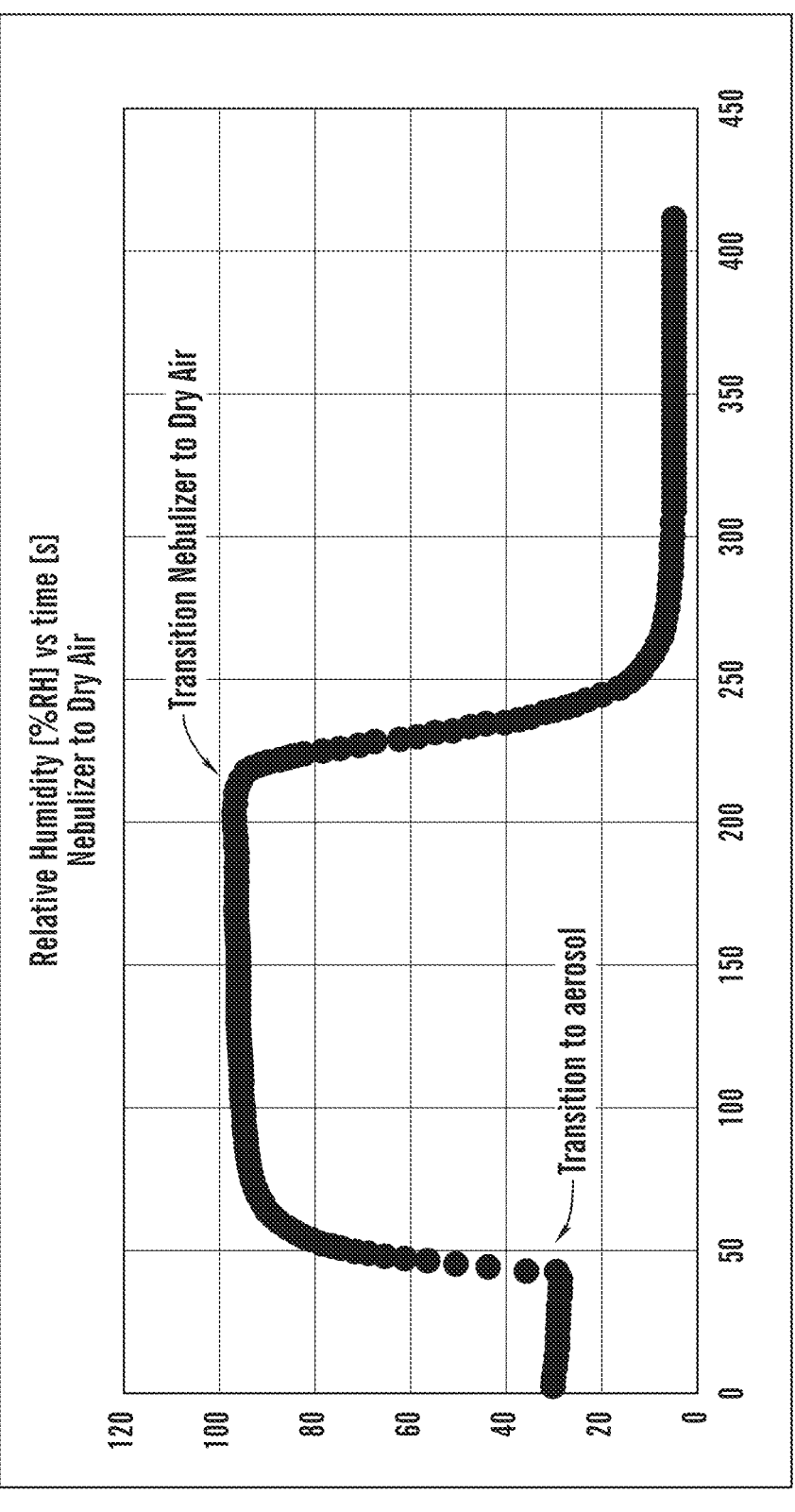
FIG. 6 is a plot of percent relative humidity vs time demonstrating the response of a humidity sensor used in an embodiment of a device for monitoring nebulizer use.

In accordance with some embodiments of the invention, the humidity sensor 250 data can be used to determine whether a proper dose or treatment occurred. In operation, the humidity in the conduit will increase as aerosolized medication flows through the conduit and contacts humidity sensor 250. For example, if the user forgets to fill the medication reservoir with a dose of liquid medication prior to using the nebulizer, a low humidity will be measured by the humidity sensor and sent to the controller 230 during that treatment session. FIG. 6 shows an example of a plot of humidity data recorded during use. In this example, prior to about 45 seconds the humidity 250 sensor is exposed to an ambient air flow (without aerosolized medication) air, between about 45 and 210 seconds the humidity sensor 250 is exposed to a flow of air containing aerosolized medicine generated by a nebulizer 10, and after 210 seconds the humidity sensor 250 is exposed to an ambient air flow (without aerosolized medication). A sharp onset or transition is seen when the humidity sensor 250 is exposed to the aerosolized medication from the nebulizer and the humidity rises over 80%. A similar sharp drop is seen when the aerosolized medication from the nebulizer is stopped and the humidity sensor 250 is exposed to relatively dry ambient air and the humidity drops significantly below 80%. In some embodiments the average ambient humidity will be high while the nebulizer is being used properly (e.g., with medicated solution), although the instantaneous humidity may oscillate up and down at least slightly (e.g., as the user inhales and exhales), the device 100 can determine that the change in measured humidity is indicative of use (e.g., by measuring a baseline humidity prior to treatment). In some embodiments, a relative humidity of greater than about 20%, 30%, 40%, 50%, 60%, 70% or 80% or more indicates that the nebulizer 10 is operating and filled with a medication, depending on the formulation of the medication to be nebulized.

In some embodiments, the monitoring of the dosage compliance of the user, in addition to being processed and saved by the controller 230, can also be communicated in real time to the user by indicators on the nebulizer monitoring device. For example, LED lights or a display can be used to identify the number of doses taken in a predefined time period. These LEDs or displays can provide real time dose/treatment information to the user.

FIG. 4A shows an array of dose indicators 1414. The dose indicators 1414 can include a window in the housing connected to one end of a light pipe 244 which will be illuminated when one or more indicator LEDs 242, mounted on PCB printed circuit board 210, are activated. The controller 230 can determine as a function of signals and/or data received from the humidity sensor 250 and/or the pressure sensors 222 when a treatment is completed (as described herein) and can illuminate one or more indicator elements 1414 appropriately, e.g., one element can be illuminated per treatment or dosage detected. In some embodiments, the indicator elements 1414, once lit up, remain on for a predetermined time (e.g., 8 or 12 hours—where treatment is every 6 hours, the dose indicator 1414 can remain illuminated for 6 hours indicating that dose was taken within the last 6 hours) or until a predetermined time is reached (e.g., 12:00 am, 2:00 am, or any time between the expected time of the last dose/treatment and the expected time of the first dose/treatment of the day, such at 6:00 am) such that indicator 1414 indicates how many doses have been completed during the course of the day and is reset (e.g., extinguished) prior to the first dose/treatment of the day. After 24 hours, the lights can then be reset e.g., turned off, and a count of dosages for another day can begin again. The indicator elements 1414 therefore can provide a method to verify count of the dosages to the user or healthcare provider, and can help support and track compliance to a nebulizer therapy. In some embodiments other indicators can be used, for example audible indicators that emit a tone when a dosage session has been completed, or vibrating elements that vibrate when the dosage session is completed.

In some embodiments more than one sensor can be used for dose compliance determination e.g., to determine both the quantity and quality use. This can help determine if a user is; (1) a regular user with good technique, (2) a regular user with poor technique, (3) an irregular user with good technique, or (4) an irregular user with poor technique. For example, a nebulizer being used with an incorrect or sub-optimal orientation, such as where the user is reclining or slumped over (e.g., the angular orientation as measured by the accelerometer 280 is not level, such as where $R_x\neq0$, see FIG. 1A) or tilting their head (e.g., the angular orientation as measured by the accelerometer 280 is not level, such as where $R_y\neq0$, see FIG. 1A), can be detected using signals received by the controller 230 from the accelerometer 280. In this situation, a flow rate would be detected if the user is breathing through the device correctly, although most likely the humidity would not reach the typical values for the amount of time expected for a nebulized material (e.g., greater than about 80% RH for the prescribed duration of the treatment) since all or a portion of the medical solution could spill out of the reservoir. In another scenario, the nebulizer might be turned on and placed on a surface (e.g., with a correct orientation according to the accelerometer 280) for part or all of the typical time duration of the treatment. Here the temperature sensor might indicate the mouthpiece was not in contact with a user for the duration of the treatment and the pressure sensor would also indicate no user breath-ing in the nebulized material for part of the time, although the humidity sensor might detect humidity. In yet another scenario, the user may have forgotten to add the medication to the nebulizer reservoir but may be otherwise using the nebulizer correctly (e.g., correct orientation, mouthpiece in place, correct breathing). In this scenario the humidity sensor would indicate that no nebulized medicine is being delivered. Therefore, combination of data from two or more sensors can be useful in providing a more robust data for use by a software based program or algorithm to use in the determination of the quantity and quality of the doses taken.

In accordance with some embodiments of the invention, the nebulizer monitoring device 100 can include one or more pressure sensors 222, humidity sensors 250, a temperature sensor 230, accelerometers or gyroscopes 280, connected to the controller 230. In operation, the controller 230 receives signals from each sensor, converts the signals to raw sensor data (e.g., using an analog to digital converter), and stores the raw sensor data in memory 233. The nebulizer moni-toring device 100 can include one or more transceivers 290 that enable the controller 230 to transmit data to remote systems (e.g., the base station 300, a personal computer, a smart phone, a cloud based system). In accordance with some embodiments of the invention, the controller 230 can transmit some or all of the raw sensor data (e.g., pressure data, humidity data, temperature data, accelerometer data, gyroscope data) to the remote system. The raw sensor data can be processed by the controller 230 and/or the remote system to create processed sensor data. For example, the pressure sensor sends a signal in the form of a voltage or current level and the voltage or current level is processed to convert it to a measure of pressure. The processed sensor data can be transmitted to the remote system along with or instead of the raw sensor data. The nebulizer monitoring system can include a real time clock that keeps track of the date and time of day or can be connected wirelessly (e.g., using WiFi, Bluetooth or ZigBee) to a date and time server that provides the controller 230 with date and time infor-mation. The controller 230 can associate the sensor raw data with a date and/or time stamp such that the controller 230 can record that date and time that the sensor raw data was received. In accordance with some embodiments, the date and time stamp can be a digital representation of the local or GMT time and date. In accordance with some embodiments, the date and time stamp can be an offset value from a predefined date and/or time (e.g., the number of seconds from midnight, Jan. 1, 1980, or the number of second from midnight of the current day). In accordance with some embodiments, the controller 230 can store, a date and/or time stamp value associated with each element (e.g., a data value or group of data values corresponding to a single data point) or group of elements of raw sensor data stored in memory. In accordance with some embodiments, the con-troller 230 can store, a date and/or time stamp value asso-ciated with each element (e.g., a data value or group of data values corresponding to a single data point) or group of elements of processed sensor data stored in memory. In accordance with some embodiments of the invention, the controller 230 can include the corresponding date and/or time stamp with any of the raw sensor data and/or processed sensor data sent to a remote system.

Figure 7B:
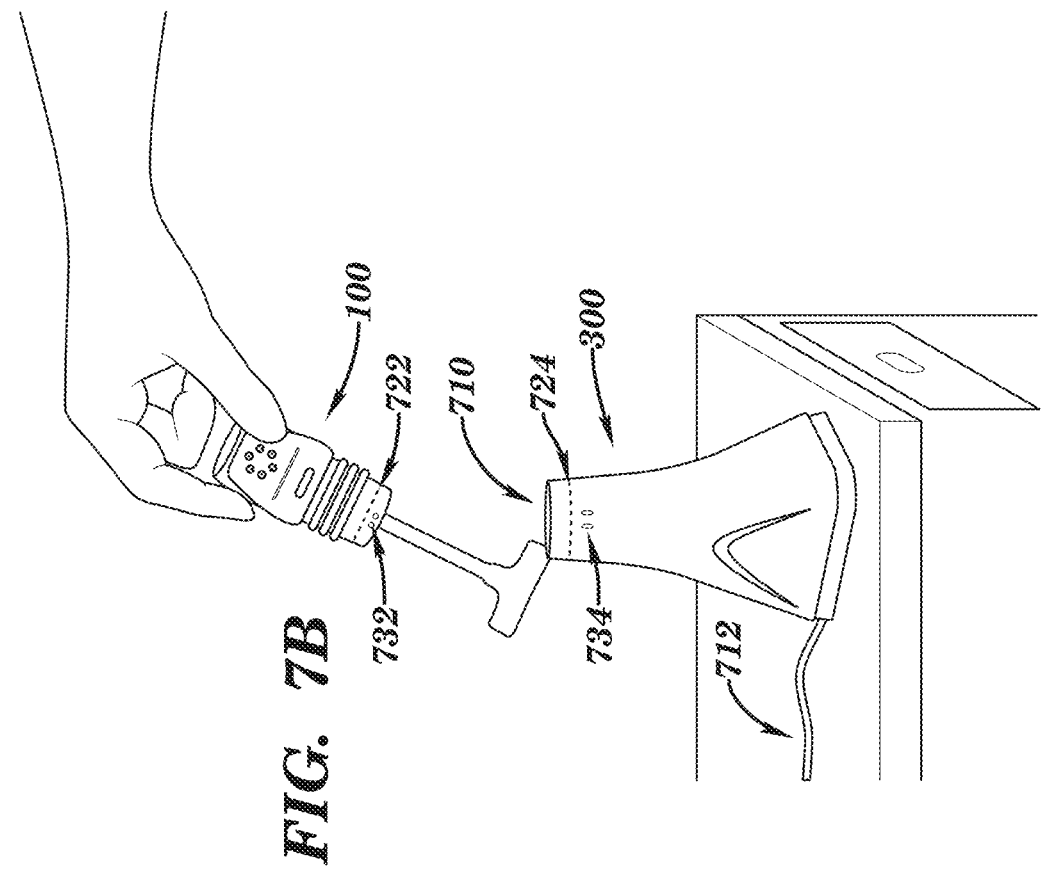
FIG. 7B shows a 3D projected view of the base station in a possible environment as it would be used.
Figure 7A:
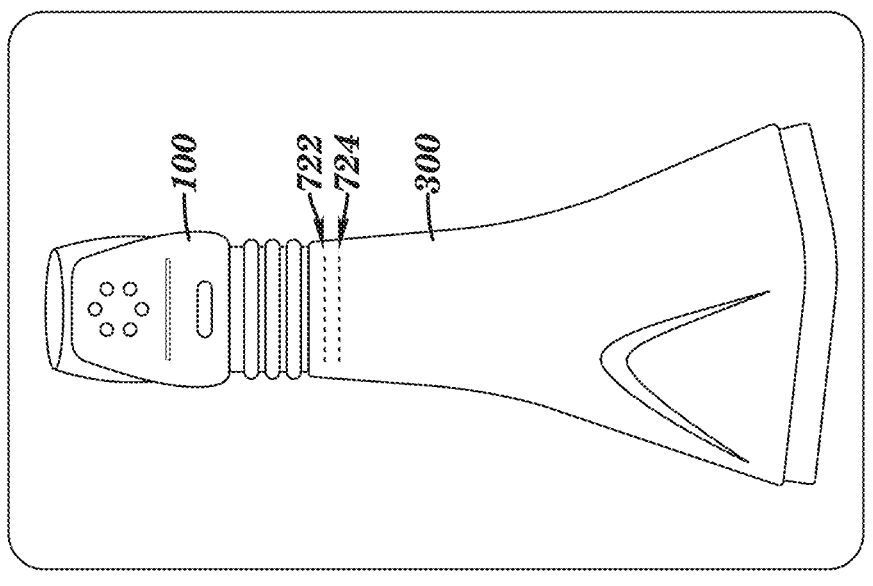
FIG. 7A is a 3D projected view showing a base station configured to receive a nebulizer monitoring device.

FIG. 7A shows an embodiment of a base station 300 that is configured to receive the nebulizer monitoring device 100 according to some embodiments of the invention. FIG. 7B shows the base station in a possible environment as it would be used, e.g., a nightstand. As depicted in these figures, the base station 300 can have a port 710 for accepting one end of the nebulizer monitoring device 100 (e.g., the inlet port or nebulizer connector 114 or the outlet port or mouthpiece connector 112). In some embodiments the base station 300 includes an electrical connection, e.g., 712, to a power supply such as a wall outlet. In some embodiments the nebulizer monitoring device 100 can include one or more batteries 260 connected to the controller 230 and a charging circuit for charging the battery, and when the nebulizer monitoring device 100 is placed on the base station 300 as shown in FIG. 7A the nebulizer monitoring device 100 can be charged. In some embodiments, the one or more batteries 260 can be wirelessly and/or inductively charged. The base station 300 and the nebulizer monitoring device 100 can each include induction coils 722, 724 for inductive charging of the battery 260 such that when the nebulizer device 100 is placed on the base station as shown in FIG. 7A, the electric field produced by the induction coil 724 of the base station 300 induces a current to flow in the induction coil 722 of the nebulizer device 100. The induction coil 722 of the nebulizer device 100 can be connected to a charging circuit that controls the flow of current to charge one or more of the batteries 260. In some alternative embodiments, the charging is through a direct electrical contact. For example, wherein the base station includes a plurality of pogo-pins 734 and the nebulizer mount includes a plurality of contact pads 732. The pogo-pins 734 and contact pads 732 make an electrical connection between the nebulizer mount and nebu-lizer monitoring device when they are combined as shown FIG. 7A, allowing electrical energy to be transferred, e.g., for charging battery 260. It is understood that other forms of contact can be made between the nebulizer monitoring device and base station for charging, for example, a USB connection, a standard two or three prong plug or an auxillary power cord.

In some embodiments, the base station 300 can include one more controllers (e.g., a central processing unit and associated memory and/or system on a chip), one or more wireless transceivers (e.g., capable of Bluetooth, WiFi, Zig-Bee, and/or cellular data communication) and the nebulizer monitoring device 100 can include a wireless transceiver 290 (e.g., also capable of Bluetooth, WiFi, ZigBee, and/or cellular data communication). The nebulizer monitoring device 100 transceiver 290 can transmit raw and processed data to the wireless transceiver of the base station 300. In some embodiments, the base station 300 can include a wireless transceiver for wireless communication with a remote system such as a smart phone or tablet, personal computer, local hub, or to the cloud.

When the nebulizer monitoring device 100 collects usage data when the nebulizer device 10 is used by a user, and the data collected from the sensors and stored in memory by the controller 230 can be wirelessly transmitted to the base station 300, for example, using Bluetooth or WiFi communication. In some embodiments, the data can be transmitted in real time, while the nebulizer device 10 is being used (e.g., including any delays due to processing of the data by the controller 230 prior to transmittal. In accordance with some embodiments, the data can be sent at a later time, for example when the nebulizer monitoring device 100 is docked or placed on the base station and while the nebulizer monitoring device 100 is charging. In some embodiments, the base station can be used to transmit data to the nebulizer monitoring device, for example, to calibrate (e.g., one or more sensors) of the nebulizer monitoring device 100, to reconfigure the settings or operation of the nebulizer monitoring device 100, or to update the firmware or software of the nebulizer monitoring device 100.

In some embodiments, a user can have more than one nebulizer monitoring device and more than one base station, for example where the monitoring device is used for a different nebulizer treatment or for a different patient or subject. In some of these embodiments, the nebulizer monitoring device can be configured to universally connect to any number of base stations for charging but can be assigned a unique identifier (e.g., in software and/or hardware, such as a MAC address or device serial number). The unique identifier can be used by software in the nebulizer monitoring device to identify the source of data (e.g., data prefixes or source identifiers for data streams sent to the cloud based systems); to determine the identify of a device placed on a base station (e.g., by software in the base station to determine where to send the data or how to charge the device); and to configure the device for its intended use (e.g., to configure the nebulizer for a specific treatment). For example, the nebulizer monitoring device, when trying to connect to a base station, can transmit a data of a unique identifier or key (e.g., a string of characters) to the base station and the base station can determine through an algorithm (e.g., a software module or program) run on the base station's CPU how to process and where to send any data received from that specific device associated with the received unique identifier. For example, the data along with the device's unique identifier can be added to a memory element and sent to a cloud based computer system for processing, or the data can be ignored e.g., or not added or sent by a specific base station. In some embodiments the base station and nebulizer monitoring device can be paired such that an indicator (e.g., visual, audible) will alert the user if the correct device is docked or being docked on the matching base station. In this embodiment, the software in the docking station can be configured to only connect to a specific nebulizer monitoring device based on the device's unique identifier (e.g., the software in the docking station can compare the device's unique identifier to on stored in memory and only connect to the device, allow data transfers and/or allow charging if the device's unique identifier matches the one in memory).

In some embodiments the nebulizer monitoring device includes memory (e.g., 233 in FIG. 2B) such as non-volatile flash data and can store data collected from the sensors for several days (e.g., at least 7 days, at least about 3 days). For example, the memory may include about 24 megabits of non-volatile data. In some embodiments, the CPU 231 only processes pressure data to provide indications of flow rate and dose (e.g., to light up LED lights) and stores other data such as humidity and temperature in memory. The stored data can be sent to a remote system and processed externally (e.g., sent to the base station or a cloud based computing system). In other embodiments, the CPU 231 can process the raw sensor data to determine calculations of humidity, tidal volumes and temperature data (with or without date and time stamp information).

In some embodiments the base station can include one or more environmental monitoring sensors to receive and store environmental sensing data. For example, one or more of a VOC sensor, a CO sensor, an Ozone sensor, a NOx sensor, a $CO_2$ sensor, a smoke sensor, a humidity sensor, a temperature sensor, and a particulate sensor. Other sensors such as mold, spore, bacterial and other toxin sensor are also contemplated. The base station can also include a controller with a CPU and memory connected to the sensors and able to receive, process, and store data received from the base station sensors.

In some embodiments the base station includes indicators such as LED lights, audible indicators for communicating to the user. For example, to communicate the environmental data collected such as the room temperature, $CO_2$ levels or particulate levels. In some embodiment indicators on the base station can communicate that the nebulizer monitoring device is properly positioned for charging, the nebulizer monitoring device is being charged, or the nebulizer monitoring device is charged and ready to use. In some embodiments indicators can show when the base station is receiving/transmitting wireless data.

Figure 8:
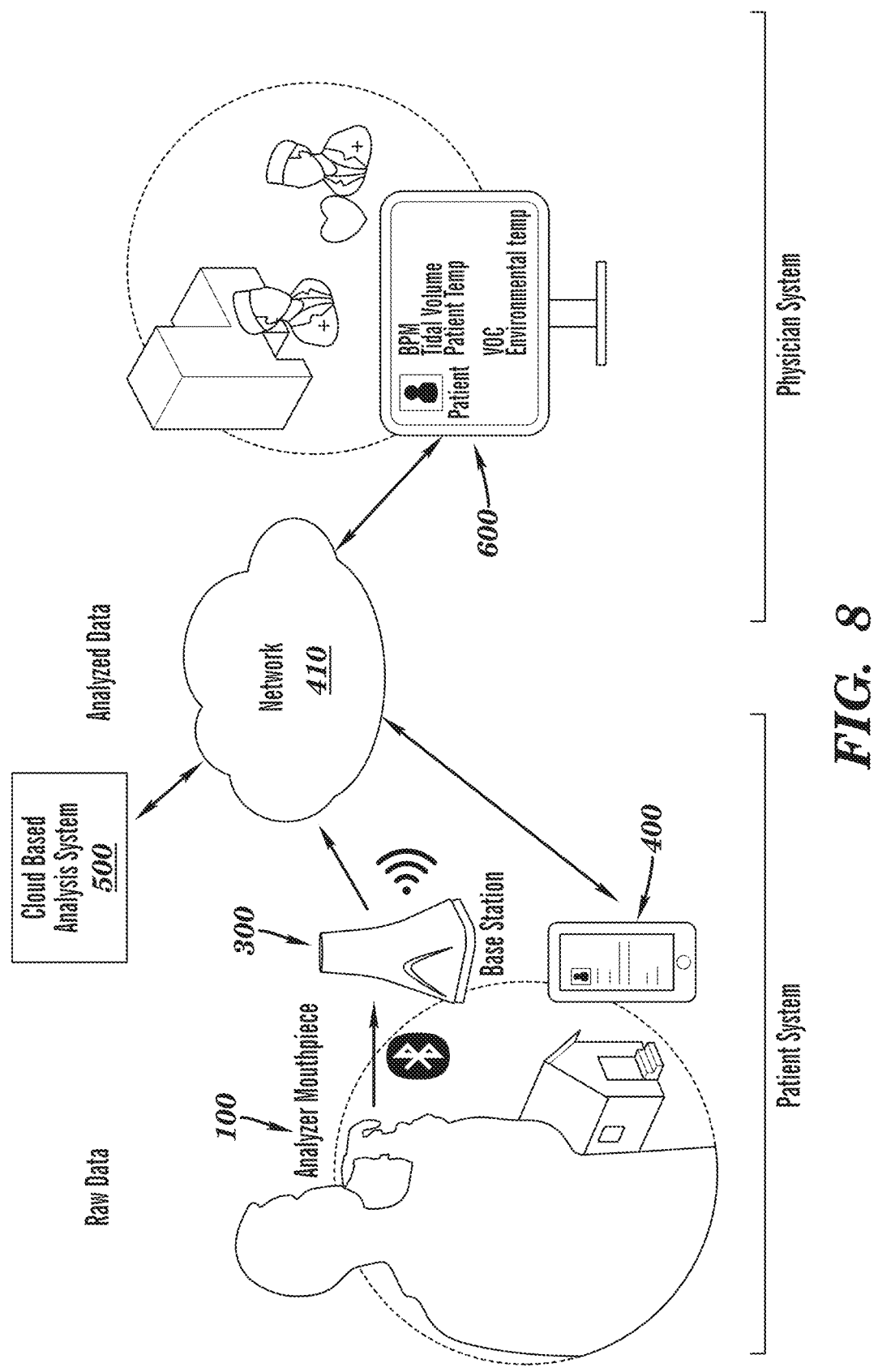
FIG. 8 is a pictorial representation of an embodiment of a system using a nebulizer monitoring device.

FIG. 8 is a diagrammatic view of a system 800 including the nebulizer monitoring device 100. The system 800 can include a user system 810 and a physician system 820. In some embodiments the user system 810 can include a user, the nebulizer monitoring device 100, the base station 300, and a smart personal device 400 such as a smart phone or tablet. In some embodiments the physician system 820 can include a data visualization system 600 such as a computer monitor and associated computers for data processing and/or visualization, and a medical professional and/or caregivers who can view data on the screen. The user and physician systems can be connected via a network 410, such as the internet or a private data network to one or more cloud based analysis systems 500. In some embodiments, the network 410 can wirelessly communicate with the smart device 400. In some embodiments, the network 410 can communicate by wire or wirelessly with the cloud system 500 and to the data visualization system 600. The cloud based analysis system 500 can receive raw and processed data from one or more nebulizer monitoring devices 100 and process and analyze the data received. The processed and analyzed data can be transmitted through the network 410 to the physician system 600.

The system depicted in FIG. 8 can be used to monitor the use and compliance of a nebulization therapy by one or more users. For example, each time a user uses the nebulizer, the nebulizer monitoring system can record the sensor data, for example in terms of pressures (e.g., flow rates), temperature of the user, humidity, orientation of the device. This data can be transmitted using network 410 to the cloud based system 500 where it can be processed or analyzed. Optionally, the analyzed data can be sent back to the user, for example to their smart device 400 to inform them e.g., through an app, that a dose was taken. In addition, the analyzed data can be used to generate messages that provide feedback to the user, such as to indicated that they are not using the nebulizer device 10 correctly (e.g., during treatment, the nebulizer device 10 was not level, the user did not take deep breaths, the user did not take enough breaths, or the user did not fill the reservoir with medication prior to use).

Figure 9:
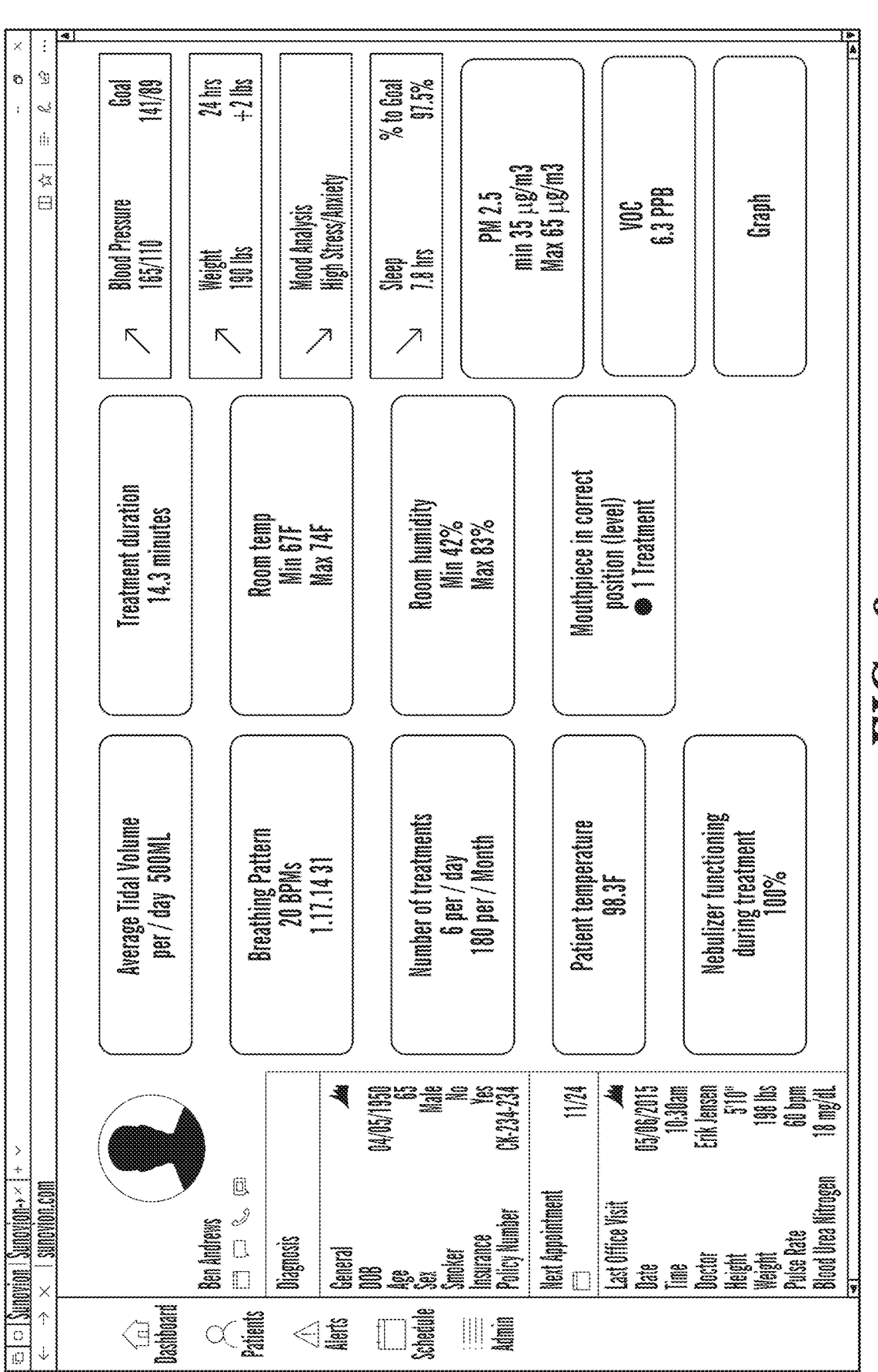
FIG. 9 shows a dashboard for viewing information provided by a system for monitoring a user's use of a nebulizer.

In some embodiments, the system can include a user dashboard 900 as shown in FIG. 9. The dashboard 900 can be displayed on any computer system, including for example, a smart phone 400 or visualization system 600. The dashboard can include information such as the average tidal volume over the treatment period and/or for the last treatment, breathing pattern (e.g., breaths per minute), number of treatments per day and/or per month, user temperature (e.g., most recent and/or average for a day, week, month or treatment period), nebulizer function, treatment duration (e.g., average time over the last week or month, or the treatment period), room temperature (e.g., maximum and minimum for the current day, for the last week or month, or the treatment period), room humidity (e.g., maximum and minimum for the current day, for the last week or month, or the treatment period), mouthpiece placement (e.g., angular orientation of the device during last use) and VOC's can be displayed.

In some embodiments, the health care provider can view the data on system 600 and make an assessment as to the quantity and quality of the dosing and health of the user over short, medium and long periods of time. The user can view this information to assess the progress of the user and to identify indicators of a potential exacerbation. The healthcare provider can view the data (e.g., remotely or with the patient) in response to a user who calls in distress and can examine the data to see if the onset of an exacerbation is occurring, and to assess possible causes (e.g., the nebulizer wasn't used correctly for the past two weeks). The healthcare provider can then prescribe an appropriate action such as recovery doses or antibiotic treatment, and if appropriate additional training to the user on the correct use of the nebulizer and mediation. Over medium to long periods of time, for example, after one, two, three, six or more months of data collection, the user meets with the healthcare provider on a scheduled visit unassociated with an exacerbation and the healthcare provider can pull up the data and advise the user as to their compliance and overall health. Long term monitoring can also provide information as to the general health of the patient, for example, where the tidal volume and breathing rate may change (e.g., show improvement by increasing or show decline by decreasing) over time. The long term monitoring also aids in establishing threshold values for the user for tidal volume and respiration rate which will typically change with time can be used by software executing on the cloud system 500 to trigger alerts. For example, after each treatment session, the treatment data can be uploaded to the cloud system 500 and specific measured or calculated values (e.g., raw data or processed) can be compared with threshold values and where the measured or calculated value is greater or less than the threshold value or the difference is greater or less than a predefined amount, the could system 500 can send a message or alert to the user, the healthcare provide or the caregiver indicating that there may be a problem with the user's care.

In some embodiments, the analysis system 500 can send an alert to the user and/or the health care provider when one or more parameters such as temperature, tidal volume, breathing rate, or humidity are above or below a threshold value. The threshold value can be set based on expected average or mean values determined from a large sample population (e.g., and adjusted based on weight, age, and other characteristics of the user) or based on historical baseline data for the user collected (e.g., over one, two, three, six or more months) using the nebulizer monitoring device 100. For example, where the value of the parameter deviates from the threshold value by more than about 5% (e.g., more than about 10%, more than about 15% or more than about 20%) and alert can be triggered. The alert can be send to different parties, depending on the amount of deviation from the set threshold value. For example, an alert can be sent to the primary caregiver when over a two or three-day period the user's temperature has risen by more than 1 degree Celsius and an alert can be sent to the healthcare provider when the over a two or three-day period the user's temperature has risen by more than 2 degrees Celsius. In another example, an alert can be sent to the primary caregiver when over a two or three-day period the user's Tidal Volume has decreased by more than about 5%, and an alert can be sent to the healthcare provider when over a two or three-day period the user's Tidal Volume has decreased by more than about 10%, which can prompt the healthcare provider to pull up the data for the user and/or contact the user and initiate corrective actions. The alert can be in the form of a phone call message, text message, e-mail message or other visual message sent to the healthcare provider.

Figure 10:
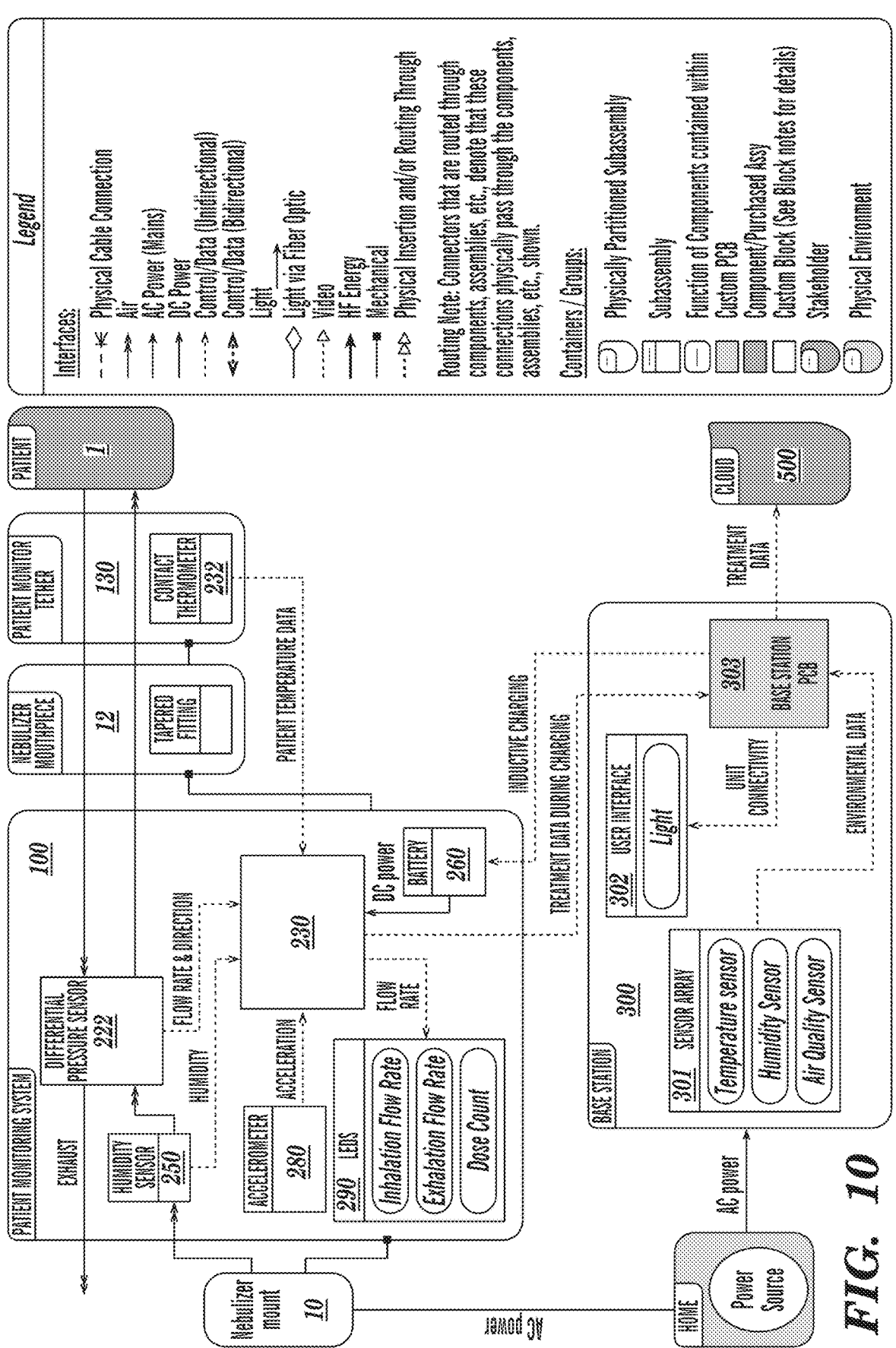
FIG. 10 shows schematically an embodiment of components for a system for monitoring a user's use a nebulizer.

FIG. 10 shows a diagrammatic view of a nebulizer monitoring system according to some embodiments of the present invention. In interacting with the system, the user 1 inhales and exhales (double headed arrows) through the nebulizer mouthpiece 12 while contacting the contact thermometer 232 which can be attached to a user monitor tether 130. The user monitor tether 130 can be mechanically and electrically connected to the user monitoring system 100 and controller 230 e.g., to transmit user temperature data from the user to controller 230. In some alternative embodiments, the user monitoring tether can be mechanically and electrically connected to the mouthpiece 12, for example to transmit temperature data from the user through the mouthpiece and to controller 230 of system 100. In FIG. 10 the double headed arrow can indicate any flow of air such as caused inhalation and exhalations of the user as well as the flow of nebulized medication. Communication, for example, through an electrical connection can include the use of a physical connection (e.g., wire, cable, USB, Aux cord) or through wireless transmission (e.g., WiFi, Bluetooth, ZigBee, and NFC).

The nebulizer mouthpiece 12 can be mechanically (e.g., press fit or snap fit or using tapered fittings) and fluidly connected to the nebulizer monitoring system 100. In some embodiments the mouthpiece is removably, mechanically and fluidly, connected to the nebulizer monitoring system 100. In some embodiments the mouthpiece 12 can be electrically connected (e.g., removably connected) to the nebulizer monitoring system 100, for example to transmit user temperature data from the user to controller 230 of the nebulizer monitoring system 100. The nebulizer monitoring system 100 can include one or more flow sensors such as differential pressure sensor 222, in the flow path of the inhalation and exhalation from the user. In some embodiments the flow sensor can include a Sensirion SDP31 differention pressure sensor (SKU 1649-1080-1-ND, DigiKey, MN). The exhalations can be exhausted out of the nebulizer monitoring system 100, for example through a one-way valve. In some embodiments, the exhalations can be exhausted after flowing past/through the flow sensors 222 and do not contact the humidity sensor 250. Other embodiments can include an exhaust value that is placed on the nebulizer mouthpiece (e.g., wherein exhalations are not detected by flow sensors 222 and humidity sensor 250), or an exhaust valve where the humidity sensor 250 is in the path of the exhalations. The differential pressure sensor element 222 can be electrically connected to controller 230 and can send flow rate and flow direction data to the controller 230 (e.g., a flow rate vector). The humidity sensor 250 can be electrically connected to controller 230 can send humidity data to controller 230. The nebulizer monitoring system 100 can also include an accelerometer 280 communicatively connected to controller 230 and which sends acceleration data to the controller 230. In some embodiments the accelerometer 280 includes an NXP Freescale ACCELEROMETER 2-8G 12C 16QFN (part number MMA8452QR1CT-ND, Digi-Key, MN). The nebulizer monitoring system 100 can include LEDs 120 and 140 and associated display elements (e.g., light pipes, widows) and can be coupled to display inhalation flow rates, exhalation flow rates and dose count. In some embodiments the LEDs include one or more Broadcom Avago Surface Mount Tricolor ChipLED 0606 (part number 516-1795-6-ND, Digi-Key, MN) and Kingbright LEDs (part number 754-2121-1-ND, Digi-Key, MN). The LEDs can be electrically connected to controller 230 to illumination signals determined as a function of flow rate data and/or humidity sensor data. The nebulizer monitoring system 100 can also include a battery 260 which is electrically connected to power controller 230, e.g., with DC electric power. In some embodiments battery 260 can be directly connected to one or more of LEDs 120 and 140, accelerometer 280, humidity sensor 250 and pressure sensors 222. In some other embodiments, the controller 230 can power one or more LEDs 120 and 140, accelerometer 280, humidity sensor 250 and pressure sensors 222 from power received from 260. In some embodiments one or more transformers can be included to provide DC or AC power to components. The transformers can be part of controller 230 or a separate component. The controller 230 can include one or more memory elements, one or more timers (e.g., hardware based timers or software based timers) and one or more microcontrollers, microprocessors, digital signal processors, and/or field programmable gate arrays. In some embodiments the controller 230 can include one or more of the following components: Microchip charge management controller (part number MCP73832T-2ACI/OTCT-ND, Digi-Key, MN), Nordic Semiconductor CPU/Bluetooth low energy Controller (part number 1490-156-1-ND, Digi-Key, MN), On Semiconductor LED Controller (part number NCP5623BMUTBGOSDKR-ND, Digi-Key, MN), Texas Instruments Voltage Regulator (part number 296-11013-1-ND, Digi-Key, MN), Kyocera AVX 32 MHz Crystal (part number 1253-1586-1-ND, Digi-Key, MN), Texas Instruments MOSFET N-CH 12V (part number 296-41412-1-ND, Digi-Key, MN), and Johanson ANTENNA CHIP 2.4 GHZ (part number 712-1005-1-ND, Digi-Key, MN). The controller 230, the LEDs 120 and 140, the accelerometer 280, the humidity sensor 250, the pressure sensors 222, and the battery can be electrically connected to and/or mounted on an a flexible or rigid printed circuit board, e.g., a PCB.

The nebulizer monitoring system 100 can be mechanically (e.g., press fit or snap fit or using tapered fittings), and optionally removably, attached to the nebulizer device 10. The nebulizer device 10 can be in fluid communication with the nebulizer monitoring system 100 such that the nebulized, aerosol medication produced by the nebulizer device flows through the nebulizer monitoring system 100 and interacts with and/or contacts one or more of the sensors (e.g., the pressure sensors 222, the humidity sensor 250 and/or a temperature sensor, not shown). In accordance with some embodiments, the medication becomes nebulized into an aerosol by nebulizer device 10, and caused to flow past humidity sensor 250 and pressure sensors 222, then through the mouthpiece 12 and into user 1 who inhales the medication. In some embodiments, the nebulizer device 10 can include an ultrasonic or a mesh nebulizer and the nebulizer device 10 can be powered by a conventional home power source (AC current from a standard 120V 60 Hz or 240V 50 Hz outlet), and converted by a conventional power transformer to provide an appropriate level of DC power (e.g., 3.0 Volts at 1 Amp). In some embodiments, the nebulizer device 10 can include a jet nebulizer and a compressor for the nebulizer which can be powered from a home outlet to supply the flow of air to the jet nebulizer element.

The system shown by FIG. 10 can also include a base station 300 which can be powered by a home power source, for example, by a standard AC outlet. The power can be distributed and transformed as needed to the elements of base station 300. The base station can include a sensor array 301 having, for example, one or more temperature sensors, one or more humidity sensors, and one or more air quality sensors. In some embodiments the air quality sensors con include one or more of a VOC sensor, a CO sensor, an Ozone sensor, NOx sensor, a $CO_2$ sensor, a humidity sensor, a temperature sensor, a particulate sensor, a mold, spore, bacterial, a smoke detector, and other toxin sensor. The base station can also include a user interface 302 including, for example indicators such as an LCD display, LED lights, speakers, and vibrating elements. The interface can also include verbal communication elements e.g., a phone or verbal monitoring and transmitting device (e.g., one or two-way radio). The base station can include a clock e.g., for displaying time or providing an alarm. The base station can also include a controller 301 including one or more CPUs, memories, timers, microcontrollers, and transceivers. The environmental sensor array 301 can be electrically connected to the controller 303 to transmit environmental data signal to the controller 303. The base station 300 can be configured for wired and/or wireless charging of the nebulizer monitoring system battery 260. In accordance with some embodiments of the invention, the base station 300 can include an induction coil for inductive charging of the battery 260 and/or can include a direct electrical connection (e.g., pogo pins, a wired power connector, a USB port, or a standard two/three prong plug) to supply power directly to the nebulizer monitoring system 100. The controller 230 of nebulizer monitoring system 100 can be electrically connected to transmit data to and receive data from the controller 303 of base station 300.

In some embodiments user data can be collected and stored in a memory element of controller 303 and transmitted to the cloud system 500 after treatment is completed, on a periodic basis, for example, hourly, daily or when the nebulizer is being charged. Alternatively, or additionally, in some embodiments, treatment data can be transmitted to the cloud system in real time, accounting for delays in transfer, from controller 230, to controller 303 and to cloud system 500. The controller 303 can also be connected to a network 410 such as the internet and be connected to the cloud system 500. In accordance with some embodiments, the nebulizer monitoring system 100 can transmit treatment data to the base station 300 and the base station 300 can transmit the treatment data over the network 410 to a remote system such as the cloud based analysis system 500. In addition, base station 300 can transmit commands and configuration data to the nebulizer monitoring system 100 and transmit data in response to the commands. The configuration can be used to control and change the operation of the nebulizer monitoring system 100 and can include new software program modules as well as updates to existing software program modules being executed by the controller 230 of the nebulizer monitoring system 100.

Figure 11:
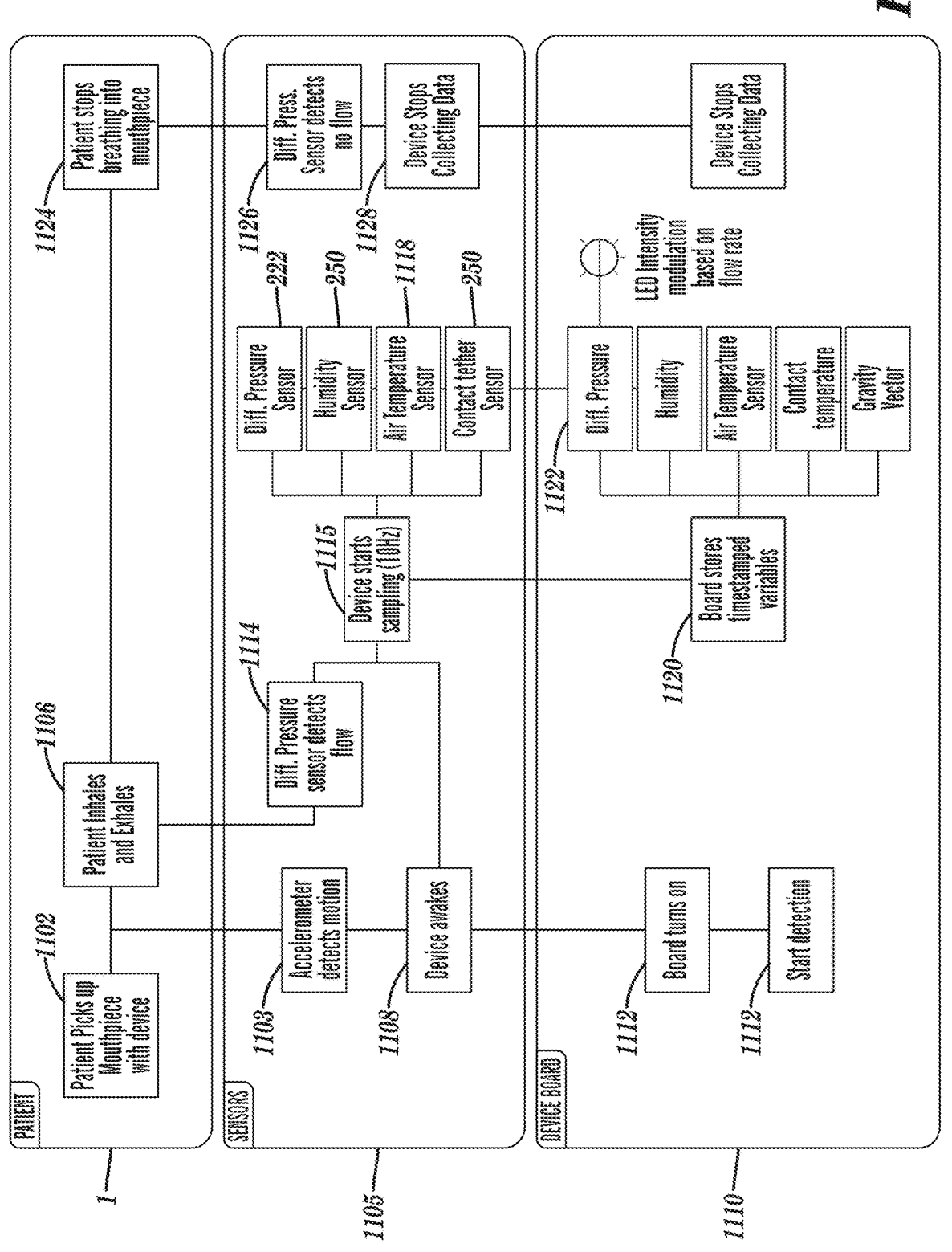
FIG. 11 shows pictorially an embodiment for steps taken when using a system for monitoring a user's use a nebulizer.

FIG. 11 shows a diagrammatic view of elements of a method of using a system for monitoring a nebulizer according to some embodiments of the invention. The user in preparation to take a dose of medication, 1101 picks up the mouth piece with the device 1102. An accelerometer 1103 in sensor system 1105 detects motion (e.g., for more than 200 ms, consistent with handling of the mouthpiece and device by a user). The detected motion thereby causes the device to awake 1108, where the device is turned on 1110 and starts detecting air flow 1112. The patent then inhales and exhales through the mouthpiece 1106. Flow of air caused by the inhalation and exhalation is then detected using a differential pressure sensor 1114 and sampling 1115 (e.g., at a rate of 10 Hz) is initiated for an array of sensors such as a differential pressure sensor 222, a humidity sensor 250, an air temperature sensor 1118, and a contact thermistor 250. The device board 1110 stores and time stamps the data received from the array of sensors 1120. The differential pressure data is displayed using an LED intensity modulation based on the flow rate 1122. At some point, e.g., when the dose is completed, the user stops breathing into the mouthpiece 1124 and the differential pressure sensor detects no flow 1126 for 1 or more seconds (e.g., 2 or more, 3 or more, 4 or more, 5 or more). The device then stops collecting data 1128 and can return to sleep mode where it monitors the accelerometer for the initiation of another dose by the user picking up the mouthpiece and device again 1102. The user can determine if a dose is complete by any means. For example, some nebulizers have indicators such as audible indicators accompanied by an automatic turn-off. Some other nebulizers such as jet nebulizers emit a sputtering sound when the medication reservoir is empty or almost empty, indicating the dose is complete.

Figure 12:
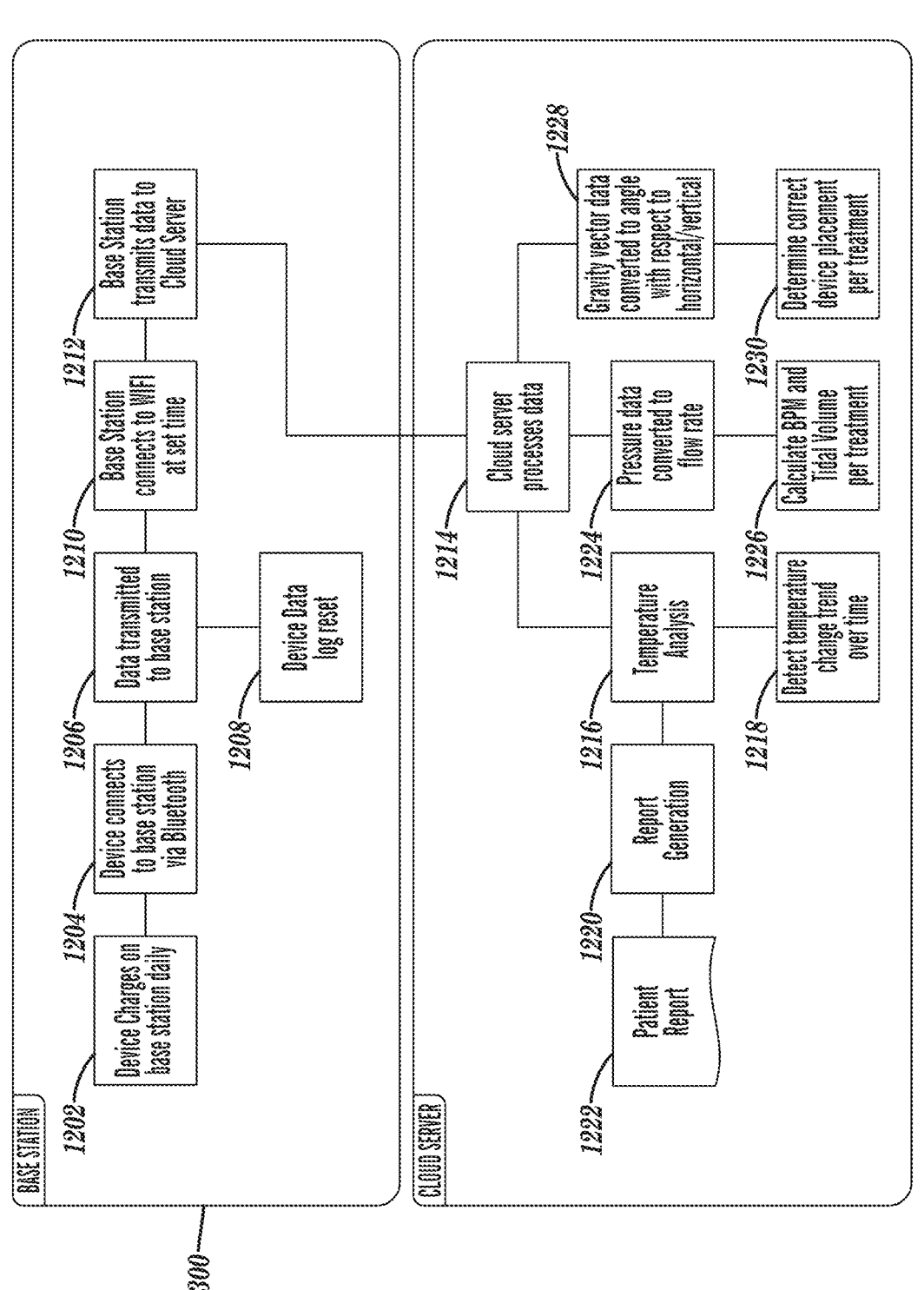
FIG. 12 show pictorially an embodiment for steps taken when using a base station and cloud server.

FIG. 12 shows diagrammatic view of elements of method of a base station and cloud server, with a system the monitors user nebulizer use parameters of pressure, temperature and accelerometer data according to some embodiments of the invention. In other embodiments other data can be monitored (e.g., humidity). The base station 300 is configured to charge the monitoring device 1202. For example, charging daily when the device is not being used by the user. While charging, the nebulizer monitoring device 100 can wirelessly connect 1204 to the base station (e.g., using Bluetooth). Thereby, data can be transmitted to the base station 1206 and the nebulizer monitoring device 100 data log can be reset 1208 (e.g., a flag can be set to indicate that the data has been offloaded to the base station 300). The base station can connect to a network such as the internet (e.g., using wired Ethernet or WiFi) at a predefined time (e.g., at midnight every day) 1210 and the base station can transmit the treatment data to the cloud server 1212. The cloud server can process the data 1214 according to one or more predefined software programs. Software executing on the cloud server can perform a temperature analysis 1216 using one or more algorithms to detect temperature changes and trends over time 1218 and generate a report 1220 which can then be provided to the user 1222. Software executing on the cloud server can process the pressure data and convert the pressure data to flow rates 1224 and determine breaths per minute (BPM), tidal volume (TV) and volume per treatment 1226. Software executing on the cloud server can process the accelerometer data to determine a gravity vector data and to calculate a user usage angle with respect to the horizontal/vertical 1228. This accelerometer derived information can be used by a care provider or an algorithm to determine if the user is holding and orienting the nebulizer device correctly during use.

The data collected using the device, methods and systems described herein can be input into an artificial intelligence system, a machine learning system or a deep learning system to provide further analysis of the user's condition. The treatment data can be combined with other user health data to assess the user's condition, including conditions related to the respiratory ailment being treated by the nebulized mediation as well as other conditions unrelated to the respiratory ailment. For example, the machine learning algorithm can receive as inputs one or more of user temperature data, tidal volume data, environmental temperature, environmental humidity, environmental air quality (e.g., particulate volume), nebulizer accelerometer data, nebulizer humidity data, and user dose data, and determine one or more conditions including user health condition, likelihood of exacerbation, and/or effectiveness of treatment.

In some embodiments, the data from the nebulizer monitoring device is simply collected, processed and provided to the healthcare provider as previously described (e.g., see dashboard shown in FIG. 9) and the provider can then review consider the data in order to ascertain an appropriate treatment or change in treatment or care. For example, a physician can contact the user and discuss and implement a course of action (e.g., reviews how to use the nebulizer, take a recovery dose, prescribes an antibiotic).

In some embodiments, a low level or rules based artificial intelligence system can be used to process the treatment data and send messages or alerts to the user or a health provider. For example, including an algorithm used by the cloud based analysis system to send an alert to the user that a dose was improperly taken or that a high temperature is detected. This system can record and determine one or more base-line physiological health metrics for the user (e.g., temperature, breathing rate and tidal volume) and a threshold can be set in a rule such that a message or an alert can be sent when a measured value exceeds the threshold.

In some embodiments, a mid-level artificial intelligence can be used. For example, this might include an algorithm used by the cloud based analysis system detecting and recognizing an exacerbation and sending alerts to the user and a physician. For example, the algorithm might detect a rising temperature for the user for more than 24 hours, a higher than baseline breathing rate and decrease in tidal volume. Therefore, in this embodiment a diagnosis is made by the system using baseline data and two or more indicators (e.g., temperature, flow rates, humidity) which the user can react to.

In some embodiments, a high-level artificial intelligence can be implemented. This can include an algorithm used by the cloud based analysis system that detects an exacerbation, determines an appropriate treatment, prescribes the treatment (e.g., alerting a pharmacy and sending instructions to a user) and altering the care-provider, insurance company and user. The artificial intelligence can also, for example, determine that the user has finished the required dose and alerts a pharmacy and/or care provider that a new prescription is required.

It is the implementation of the methods, devices and systems described herein that provides a rich and diverse set of data for various uses of a nebulizer that allows the development of artificial intelligence to monitor and aid in the care of a user using the nebulizer. Of course, since such data may be very sensitive in terms of privacy, appropriate implementations include security of the individual data, but the ability to share the data as needed. For example, a cloud network data set based on blockchain infrastructure, which will ensure that the data collected is transparent, secure, and accessible to all relevant parties.

Embodiments of the various aspects described herein can be illustrated by the following numbered paragraphs.

1. 1. A nebulizer monitoring device comprising;
    a first connector adapted to engage a nebulizer mount,
    a second connector adapted to engage a nebulizer mouthpiece,
    a conduit having an inner surface forming a fluid connection between the first connector and second connector,
    a flow sensor disposed in the conduit and between the first connector and the second connector, and configured to measure a flow rate vector of fluid in the conduit, and
    at least one indicator connected to the flow sensor,
    at least one controller connected to the flow sensor and the first indicator
    whereby at least one dimension of the at least one indicator changes as a function of a measured flow rate vector.

2. The device according to paragraph 1, wherein the at least one indicator includes at least one light source.

3. The device according to paragraph 2, wherein the change in the dimension of the at least one indicator includes a change in intensity of light emitted from the at least one light source.

4. The device according to paragraph 3, wherein the at least one light source comprises a first light emitting diode (LED) and the change in intensity of light emitted by the first LED changes as function of the measured fluid flow rate vector.

5. The device according to paragraph 4, wherein the at least one indicator includes a second LED light having a different color than that of the first LED light and the first light is illuminated when the measured fluid flow rate vector is in a first direction, and the second light is illuminated when the measured fluid flow rate vector is in a second direction.

6. The device according to paragraph 2, wherein the at least one light source comprises at least two light emitting diodes (LEDs) and a change in the dimension of the at least one indicator includes a change in the state of at least one of the two LEDs. For example, wherein the "state" can mean: on or off, a perceived lengthening or moving of the light (e.g., the speed of the lights moving over a line or in a circle), a specific set of lights in an array turning on or off in a pattern, or even flashing of lights. The state can also refer to changes in intensity.

7. The device according to paragraph 6, wherein the at least one light source includes an array of LEDs that are illuminated in sequence such that the indicator is perceived as a lengthening indicator and the perceived lengthening is a function of the measured flow rate vector, and wherein a direction of lengthening indicates the vector direction of the measured flow rate vector.

8. The device according to any one of paragraphs 1-7, wherein the first indicator comprises an audible indicator comprising at least one sound emitting device.

9. The device according to paragraph 8, wherein the dimension of the audible indicator is one or more of amplitude, frequency and pattern of sound emitted by the at least one sound emitting device. For example, the sound can change from loud to soft, soft to loud, low to high, high to low, the sound can emit beeping that changes in duration and/or frequency, the sound can emit two or more sounds that are perceived as being simultaneously emitted (e.g., a chord), the sound can also be musical (e.g., a song or song snippet).

10. The device according to any one of paragraphs 1-9, wherein the first indicator comprises a tactile indicator comprising one or more of vibrating devices, radiant heat devices and topography changing devices. For example providing a tactile sense of vibration when the device is held and, for example, a dose is complete. For example, including a display that can be read by the visually impaired (e.g., braille).

11. The device according to paragraph 10, wherein the tactile indicator includes a vibrating device and the dimension of the audible indicator includes one or more of intensity and frequency of a vibration.

12. The device according to any one of paragraphs 1-11, wherein the flow sensor includes a differential pressure sensor or a flow meter.

13. The device according to any one of paragraphs 1-12, further comprising a humidity sensor disposed in or connected to the conduit between the nebulizer mount and the mouth piece and configured to measure humidity in the conduit;
    whereby at least one dimension of the at least one indicator changes as a function of the measured flow rate vector and the measured humidity from the humidity sensor.

14. The device according to any one of paragraphs 1-13, further comprising a usage indicator including an array of light emitting diodes (LEDs) connected to the at least one controller, wherein the at least one controller is configured to:
    turn off all LEDs of the usage indicator at a predefined time;
    turn on one LED of the usage indicator in a predefined order after the controller receives a plurality of measured flow rate vectors from the flow sensor for a predefined minimum time followed by a measure of no flow rate vector by the flow sensor for a predefined time.

15. The device according to paragraph 14, wherein the usage indicator is a visual indicator comprising an array of LED lights wherein each dose taken after a designated start time is indicated by a sequential illumination of an LED in the array, and the array is reset by turning off of all of the LEDs at a predefined time of day.

16. The device according to any one of paragraphs 1-15, further comprising a humidity sensor disposed in or connected to the conduit between the nebulizer mount and the mouth piece and configured to measure humidity in the conduit and transmit a measure of humidity in the conduit to the at least one controller; and a usage indicator including an array of light emitting diodes (LEDs) connected to the at least one controller, wherein the at least one controller is configured to:

turn off all LEDs of the usage indicator at a predefined time;

turn on one LED of the usage indicator in a predefined order after the controller receives measured flow rate vectors indicating flow in the conduit, and the controller receives a plurality of measures of humidity over a predefined amount of time and wherein the average of the plurality of measures of humidity over the predefined time is above a predefined threshold.

17. The device according to paragraph 16, wherein the usage indicator is a visual indicator comprising an array of LED lights wherein each dose taken after a designated start time is indicated by a sequential illumination of an LED in the array, and the array is reset by turning off of all of the LEDs at a predefined time of day.

18. The device according to paragraph 16, wherein the threshold is a relative humidity of 80%.

19. The device according to any one of paragraphs 1-18, further comprising a temperature sensor configured to contact at least one lip of a user, when the device is in use for administering a medication to the user, and wherein the at least one controller is connected to the temperature sensor.

20. The device according to paragraph 19, wherein the temperature sensor is disposed at a first end of the mouthpiece that is configured for insertion in the user's mouth, such that when the user inserts the mouthpiece into their mouth, the temperature sensor is positioned to measure a temperature of at least a portion of the user's lip.

21. The device according to paragraph 19, wherein the second connector extends along a first axis and further comprising an arm extending along the first axis outside the conduit such that the arm extends along the mouthpiece when the mouthpiece is connected to the second connector; and wherein a first portion of the arm includes the temperature sensor, and a second portion of the arm is connected to the conduit and connects the temperature sensor to the at least one controller.

22. The device according to paragraph 21, wherein first portion of the arm is configured to align with the mouthpiece such that the first portion of the arm contacts at least a portion of the user's lip when the user inserts the mouthpiece into their mouth.

23. The device according to paragraph 21, wherein the arm includes a hinge connecting the arm to the conduit or wherein the arm is flexible and the first portion is configured to attach to the mouthpiece when the device is being used 24. The device according to paragraph 19, wherein the temperature sensor includes a thermistor.

25. The device according to any one of paragraphs 1-24, further comprising an accelerometer connected to the at least one controller.

26. The device according to any one of paragraphs 1-25, further comprising a battery connected to the at least one controller, and a charging circuit for charging said battery.

27. The device according to paragraph 26, wherein the battery charging circuit includes an induction coil configured for inductive charging.

28. A system for nebulizer use comprising;
the nebulizer monitoring device according to any one of paragraphs 1-27, and
a base station in in wireless communication with the nebulizer monitoring device.

29. The system according to paragraph 28, wherein the nebulizer monitoring device includes a battery connected to the at least one controller, and a charging circuit for charging said battery; and the base station includes a port configured to receive the nebulizer monitoring device and for charging of the nebulizer monitoring device.

30. The system according to paragraph 28 or 29, wherein the base station includes an induction coil and the nebulizer monitoring device includes an induction coil such that when the nebulizer monitoring devices is received by the base station, the base station inductively charges the nebulizer monitoring device.

31. The system according to any one of paragraphs 28-30, wherein the base station includes a plurality of pogo-pins and the nebulizer monitoring device includes a plurality of electric contact pads, such that when the nebulizer monitoring devices is received by the base station, at least two pogo-pins of the base station make contact with two contact pads of the nebulizer monitoring device and transfer electrical energy to the nebulizer monitoring device to charge the battery.

32. The system according to any one of paragraphs 28-31, wherein the base station includes at least one environmental monitoring sensor and a controller connected to the at least one environmental monitoring sensor configured to receive and store environmental sensor data from the at least one environmental monitoring sensor.

33. The system according to paragraph 32, wherein the at least one environment monitoring sensor includes at least one of a VOC sensor, a $CO_2$ sensor, a humidity sensor, a temperature sensor, mold sensor, pollen sensor, spore sensor, bacteria sensor and a particulate sensor. The system according to paragraph 32, wherein the environmental monitoring sensor is a VOC sensor. The system according to paragraph 32, wherein the environmental monitoring sensor is a $CO_2$ sensor. The system according to paragraph 32, wherein the environmental monitoring sensor is a humidity sensor. The system according to paragraph 32, wherein the environmental monitoring sensor is temperature sensor. The system according to paragraph 32, wherein the environmental monitoring sensor is particulate sensor.

34. The system according to any one of paragraphs 28-33, wherein the base station includes a network interface such that the base station can transfer data to a remote computer system.

35. The system according to paragraph 34, wherein the remote computer system includes at least one processor and associated member and is configured to receive and store data from the base station.

36. A method for administering to a user a nebulized medication, the method comprising administering a nebulizer therapy regime of a prescribed dosage of said medication using a nebulizer that includes the device of any one of paragraphs 1-27 or the system of any one of paragraphs 28-35.

37. The method according to paragraph 36, wherein the user is a patient in need of a nebulized medication and is at a high risk of non-compliance to the nebulizer therapy regime.

38. The method according to paragraph 36 or 37, wherein the user is a subject in a drug study or drug trial.

39. The method according to any one of paragraphs 36-38, wherein one or more usage indicators are stored in electronic form.

40. The method according to paragraph 39, wherein the one or more usage indicators are displayed on a data visualization system and a care provided or the user views the one or more indicators on the visualization system and if one or more indicators is indicative of an incorrect use of the device, a corrective action is taken.

41. The method according to paragraph 39, wherein the one or more usage indicators are displayed on a data visualization system and a care provider views the one or more indicators and if one of more indicators is indicative of an exacerbation, the care provider initiates a corrective action.

42. The method according to paragraph 39, wherein the usage indicators are selected from the group consisting of temperature, respiration rate, tidal volume, dosage and orientation of the device, and combinations thereof 43. The method according to paragraph 42, wherein the each of the usage indicators comprise a plurality of usage indicators which are time stamped.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed is:

1. A nebulizer system comprising:
   a nebulizer monitoring device comprising one or more sensors; and
   a device controller and/or a remote system, wherein the one or more sensors are operably coupled to the device controller and/or remote system,
   wherein:
      the device is configured to engage a nebulizer and configured to be used by a subject to receive nebulized medication;
      the nebulizer system is configured to collect data from the one or more sensors while the subject receives the nebulized medication and to determine, via the device controller and/or the remote system, a respiration rate of the subject or a temperature of the subject, together with a tidal volume of the subject;
      the nebulizer system, via the device controller and/or the remote system, is configured to compare the determined respiration rate of the subject with a previously determined respiration rate of the subject or to compare the determined temperature of the subject with a previously determined temperature of the subject, and to compare the determined tidal volume of the subject with a previously determined tidal volume of the subject; and
      based on the comparison, the nebulizer system, via the remote system and/or one or more transceivers, is configured to send a signal to at least one of the subject and a provider.

2. The nebulizer system according to claim 1 wherein the nebulizer comprises a COPD medication.

3. The nebulizer system according to claim 1, wherein the nebulizer system, based on the comparison, sends the signal to at least one of the subject and the provider if the respiration rate is less than the previously determined respiration rate or the respiration rate is greater than the previously determined respiration rate.

4. The nebulizer system according to claim 1, wherein the nebulizer system, based on the comparison, sends the signal to at least one of the subject and the provider if the respiration rate is less than the previously determined respiration rate by a first predefined amount or the respiration rate is greater than the previously determined respiration rate by a second predefined amount.

5. The nebulizer system according to claim 1, wherein the nebulizer system, based on the comparison, sends the signal to at least one of the subject and the provider if the tidal volume is less than the previously determined tidal volume or the tidal volume is greater than the previously determined tidal volume.

6. The nebulizer system according to claim 1, wherein the nebulizer system, based on the comparison, sends the signal to at least one of the subject and the provider if the tidal volume is less than the previously determined tidal volume by a first predefined amount or the tidal volume is greater than the previously determined tidal volume by a second predefined amount.

7. The nebulizer system according to claim 1, wherein the nebulizer system, based on the comparison, sends the signal to at least one of the subject and the provider if the temperature is less than the previously determined temperature or the temperature is greater than the previously determined temperature.

8. The nebulizer system according to claim 1, wherein the nebulizer system, based on the comparison, sends the signal to at least one of the subject and the provider if the temperature is less than the previously determined temperature by a first predefined amount or the temperature is greater than the previously determined temperature by a second predefined amount.

9. The nebulizer system according to claim 1, wherein the previously determined respiration rate is one of the subject's normal, baseline, mean, average or threshold respiration rate.

10. The nebulizer system according to claim 1 wherein the previously determined tidal volume is one of the subject's normal, baseline, mean, average or threshold tidal volume.

11. The nebulizer system according to claim 1, wherein the previously determined temperature is a previously determined temperature value of the subject or a temperature threshold.

12. The nebulizer system according to claim 1, wherein the one or more transceivers of the nebulizer monitoring device are configured to transmit the sensor data to the remote system; wherein the remote system is configured to:

perform the determining, comparing and sending operations of the nebulizer system.

13. The nebulizer system according to claim 12, wherein the one or more transceivers of the nebulizer monitoring device is configured to transmit the sensor data to a smart device and the smart device is configured to transmit the sensor data to the remote system.

14. The nebulizer system according to claim 12, wherein the one or more transceivers of the nebulizer monitoring device is configured to transmit the sensor data to a base station and the base station is configured to transmit the sensor data to the system.

15. The nebulizer system according to claim 14, wherein the nebulizer monitoring device further comprises a battery and the base station is configured to transfer electrical energy to the nebulizer monitoring device to charge the battery.

16. The nebulizer system according to claim 14, wherein the base station comprises at least one indicator configured to provide information based on the data from the one or more sensors.

17. The nebulizer system according to claim 1, wherein the nebulizer monitoring device further comprises a mouthpiece and the one or more sensors comprises a temperature sensor, and the temperature sensor is disposed at a first end of the mouthpiece such that when the subject inserts the mouthpiece into their mouth, the temperature sensor is positioned to measure the temperature of at least a portion of the subject's lip.

18. The nebulizer system according to claim 1, wherein the one or more sensors comprises a flow sensor that is configured to measure a flow of the nebulized medication from the nebulizer to the subject.

19. The nebulizer system according to claim 1, wherein the nebulizer monitoring device further comprises at least one indicator configured to provide information based on the data from the one or more sensors.

20. The nebulizer system according to claim 19, wherein the information relates to an exacerbation condition of the subject.

21. The nebulizer system according to claim 19, wherein the information relates to inhalation and/or exhalation of the subject.

22. The nebulizer system according to claim 19, wherein the information relates to treatment of the subject by the nebulizer.

23. The nebulizer system according to claim 19, wherein the information relates to dosage of a medicament delivered to the subject by the nebulizer.

24. The nebulizer system according to claim 19, wherein the information relates to use of the nebulizer by the subject.

25. The nebulizer system according to claim 19, wherein the information relates to a flow rate.

26. The nebulizer system according to claim 19, wherein the information relates to the tidal volume, the temperature and/or the respiration rate of the subject.

27. The nebulizer system according to claim 19, wherein the indicator comprises one or more of a visual indicator, an audible indicator, a vibrating element and a tactile indicator.

28. A method of treating a subject comprising:

providing a nebulizer system, the nebulizer system including a nebulizer monitoring device adapted to be connected to a nebulizer;

connecting the nebulizer monitoring device to the nebulizer;

the nebulizer monitoring device including one or more sensors and measuring a respiration rate of the subject or a temperature of the subject, together with a tidal volume of the subject; and the nebulizer system storing and processing the respiration rate of the subject or the temperature of the subject, together with the tidal volume of the subject;

wherein:

the nebulizer system comparing the measured respiration rate of the subject with a previously determined respiration rate of the subject or comparing the measured temperature of the subject with a previously determined temperature of the subject, and comparing the measured tidal volume of the subject with a previously determined tidal volume of the subject, and, based on the comparisons, sending a signal to at least one of the subject and a provider.

* * * * *